United States Patent [19]

Mjalli et al.

[11] Patent Number: 5,770,620

[45] Date of Patent: Jun. 23, 1998

[54] ARYL ACRYLIC ACID DERIVATIVES USEFUL AS PROTEIN TYROSINE PHOSPHATASE INHIBITORS

[75] Inventors: Adnan M. M. Mjalli, Vista; Xiaodong Cao, Carlsbad; Edmund J. Moran, Cardiff, all of Calif.

[73] Assignee: Ontogen Corporation, Carlsbad, Calif.

[21] Appl. No.: 543,630

[22] Filed: Oct. 16, 1995

[51] Int. Cl.$^6$ .................. A61K 31/405; C07D 209/18
[52] U.S. Cl. .................. 514/415; 514/466; 514/471; 514/506; 514/563; 548/495; 549/441; 549/450; 560/42; 562/448
[58] Field of Search .................. 514/563, 506, 514/471, 415, 466; 548/495; 549/441, 450; 560/42; 562/448

[56] References Cited

U.S. PATENT DOCUMENTS

| | | |
|---|---|---|
| 4,920,131 | 4/1990 | Huang et al. . |
| 5,017,610 | 5/1991 | Imaki et al. . |
| 5,025,006 | 6/1991 | DiNinno et al. . |
| 5,132,422 | 7/1992 | DiNinno et al. . |
| 5,157,033 | 10/1992 | DiNinno et al. . |
| 5,206,392 | 4/1993 | Dean ........................... 549/261 |
| 5,208,229 | 5/1993 | Schmitt . |
| 5,208,328 | 5/1993 | DiNinno et al. . |
| 5,214,139 | 5/1993 | DiNinno et al. . |
| 5,336,681 | 8/1994 | Imaki et al. . |

FOREIGN PATENT DOCUMENTS

| | | |
|---|---|---|
| 0405774 | 1/1991 | European Pat. Off. . |
| 93/23041 | 11/1993 | WIPO . |
| 94/15954 | 7/1994 | WIPO . |
| 95/02566 | 1/1995 | WIPO . |

OTHER PUBLICATIONS

Abbas, et al. "Cellular and Molecular Immunology" (1991) pp. 99–104 W.B. Saunders Co., Phila. PA.

Chernoff et al. "Cloning of a cDNA for a major human protein–tyrosine–phosphatase" Proc. Natl. Acad. Sci. USA vol. 87 pp. 2735–2739, Apr. 1990.

Bliska et al. "Tyrosine phosphate hydrolysis of host proteins by an essential Yersinia virulenc determinant" Proc. Natl. Acad. Sci. USA vol. 88, pp. 1187–1191, Feb. 1991.

Fischer et al. "Protein Tyrosine Phosphatases: A Diverse Family of Intracellular and Transmembrane Enzymes" Science vol. 253, pp. 401–406 26 Jul. 1991.

Flint, et al. "Multi–site phosphorylation of the protein tyrosine phosphatase, PTP1B: identification of cell cycle regulated and phorbol ester stimulated sites of phosphorylation" The EMBO Journal vol. 12, pp. 1937–1946, 1993.

Ghosh et al. "Suramin, an Experimental Chemotherapuetic Drug, Irreversibly Blocks T Cell CD45–Protein Tyrosine Phosphatase In Vitro" Biochemical and Biophyiscal Research Communications vol. 194, No. 1, 1993 Jul., pp. 36–44.

Hunter et al. "Protein–Tyrosine Kinases" Ann. Rev. Biochem. pp. 897–930 (1985) vol. 54.

Klarlund et al. "Transformation of Cells by an Inhibitor of Phosphatases Acting on Phosphotyrosine in Proteins" Danish Cancer Society (1984) pp. 707–717.

Knorr et al. "New Coupling Reagents in Peptide Chemistry" Tetrahedron Letters, vol. 30, No. 15, pp. 1927–1930 (1989).

MacKintosh et al. "Inhibitors of Protein Kinases and Phosphatases" *TIBS* 19–Nov. 1994 pp. 444–448.

Kishihara et al. "Normal B Lymphocyte Development but Impaired T Cell Maturation in CD45–Exon6 Protein Tyrosine Phosphatase–Deficient Mice" Cell vol. 74, pp. 143–156 Jul. 16, 1993.

Posner et al. "Peroxovanadium Compounds" Journal of Biological Chemistry, vol. 269, No. 6 pp. 4596–4604 Feb. 1994.

Trowbridge et al. "CD45: An Emerging Role as a Protein Tyrosine Phosphatase Required for Lymphocyte Activation and Development" Annu. Rev. Immunol, 1994 12:85–116.

Ugi et al. "Multicomponent reations in organic chemistry" Endeavour, New Series, vol. 18, No. 3, 1994 (No page #s).

Levitzki et al. "Tyrosine Kinase Inhibition: An Approach to Drug Development" Science vol. 267 Mar. 24, 1995.

Tonks et al. "Purification of the Major Protein–tyrosine–phosphatases of Human Placenta" The Journal of Biological Chemistry vol. 263, No. 14 pp. 6722–6730 May, 1988.

Zanke et al. "Cloning and expression of an inducible lymphoid–specific, protein tyrosine phosphatase (HePTPase)" Eur. J. Imm. 1992, 22:235–239.

Wiener et al. "Overexpression of the Protein Tyrosine Phosphatase PTP1B in Human Breast Cancer: Association With Protein Expression" Journal of the Nat'l Cancer Inst., vol. 86, No. 5 (1994) pp. 372–378.

Imbert et al. "Induction of tyrosine phosphorylation and T–cell activation by vanadate perozide, an inhibitor of protein tryosine phosphatases" Biochem J. (1994) vol. 297 pp. 163–173.

Hoppe et al. "Expression, purification and crystallization of human phophotyrosine phosphatase 1B" Eur. J. Biochem. 223, 1069–1077 (1994).

Barford et al. "Crystal Struture of Human Protein Tyrosine Phosphatase 1B" Science, vol. 263, Mar. 11, 1994 pp. 1397–1404.

Burke et al. "Potent Inhibition of Insulin Receptor Dephosphorylation By a Hexamer Peptide Containing the Phosphotyrosyl Mimetic $F_2Pmp$" Biochemical and Biophysical Research Communications vol. 24, No. 1(1994) pp. 129–134.

Shenolikar et al. "Protein Serine/Threonine Phosphatases" Annu. Rev. Cell Biol. 1994, 10:55–86.

Sun et al. "Inhibition of Ras–Induced DNA Synthesis by Expression of the Phosphatase MKP–1" Science, vol. 266, Oct. 14, 1994 pp. 285–288.

(List continued on next page.)

*Primary Examiner*—Johann Richter
*Attorney, Agent, or Firm*—Frank S. Chow

[57] ABSTRACT

The present invention provides novel protein tyrosine phosphatase modulating compounds having an aryl acrylic acid structure, compositions comprising the compounds, and methods of making and using the same.

27 Claims, 5 Drawing Sheets

OTHER PUBLICATIONS

Marshall, C.J. "Specificity of Receptor Tyrosine Kinase Signaling: Transient versus Sustained Extracellular Signal–Regulated Kinase Activation" *Cell* vol. 80, 179–185 Jan. 27, 1995.

Hunter "Protein Kinases and Phosphatases: The Yin and Yang of Protein Phosphorylation and Signaling" Cell, vol. 80, 225–236, Jan. 27, 1995.

Rink "Solid–Phase Synthesis of Protected Peptide Fragments using a Trialkoxy–Diphenyl–Methylester Resin" Tetrahedron Letters, vol. 28, No. 33, pp. 3787–3790, 1987.

Barford et al. "Purification and Crystallization of the Catalytic Domain of Human Protein Tyrosine Phosphatase 1B Expressed in *Escherichia coli*" J. Mol. Biol. (1994) vol. 239, pp. 726–730.

Inoue et al. "Fungal Metabolites Part II" Journal of Antibiotics Feb. 1994, vol. 47 No. 2, pp. 208–214.

Burke et al. "Nonhydrolyzable Phosphotyrosyl Mimetics for the Preparation of Phosphatase–Resistan SH2 Domain Inhibitors" Biochemistry 1994, 33, pp. 6490–6494.

Li, W. et al. "A New Function for a Phosphotyrosine Phosphatase: Linking GRB2–SOs to a Receptor Tyrosine Kinase" Molecular and Cellular Biology, Jan. '94 pp. 509–517.

Berger et al. "Leukocyte Common Antigen (CD45) is Required for Immunoglobulin E–mediated Degranulation of Mast Cells" J. Exp. Med., vol. 180 Aug. 1994 pp. 471–476.

Cicirelli, et al. "Microinjection of a protein–tyrosine–phosphatase inhibits insulin action in *Xenopus oocytes*" Proc. Natl. Acad. Sci. USA vol. 87, pp. 5514–5518, Jul. 1990.

Charbonneau et al. "Human placenta protein–tyrosine–phosphatase: Amino acid sequence and relationship to a family of receptor–like proteins" Proc. Natl. Acad. Sci. USA, vol. 86, pp. 5252–5256, Jul. 1989.

Bollen et al. "The Structure, Role, and Regulation of Type 1 Protein Phosphatases" Critical Reviews in Biochemistry and Molecular Biology, 27(3):227–281 (1992).

Cohen "Signal integration at the level of protein kinases, protein phosphatases and their substrates" *TIBS* 17, Oct. 1992 pp. 408–413.

Wiener, et al. "Overexpression of the tyrosine phosphatase PTP1B is associated with human ovarian carcinomas" Am. J. Obstet Gynecol vol. 170, No. 4 pp. 117–1183 (1994).

Cao, X. et al., Bioorganic & Medicinal Chemistry Letters, vol. 5, No. 24, pp. 2953–2958, (1995).

Arena, G. et al., J. Chem. Soc. Perkin 2, (1993), (10) pp. 1941–1945.

Crump, R.A.N.C. et al, J. Chem. Soc. Perkin 1, (1992) (24) pp. 3277–3294.

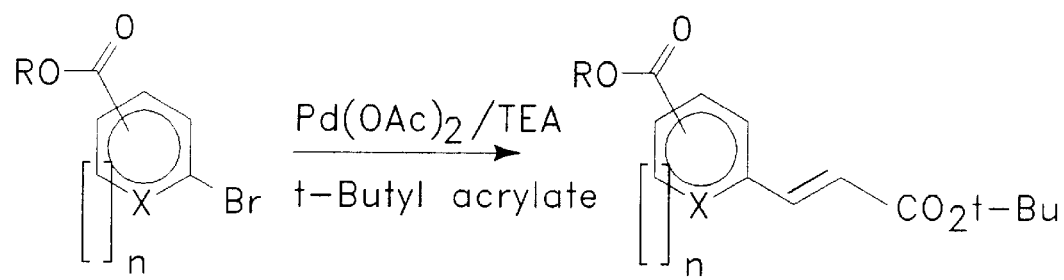
R=H or Me
n=1, X=CH or N; or
n=0, X=O or S
(1)    (2)
When R=Me | LiOH
            Dioxane/water
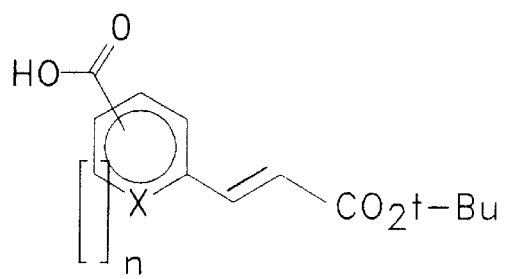
(3)
FIG. 3

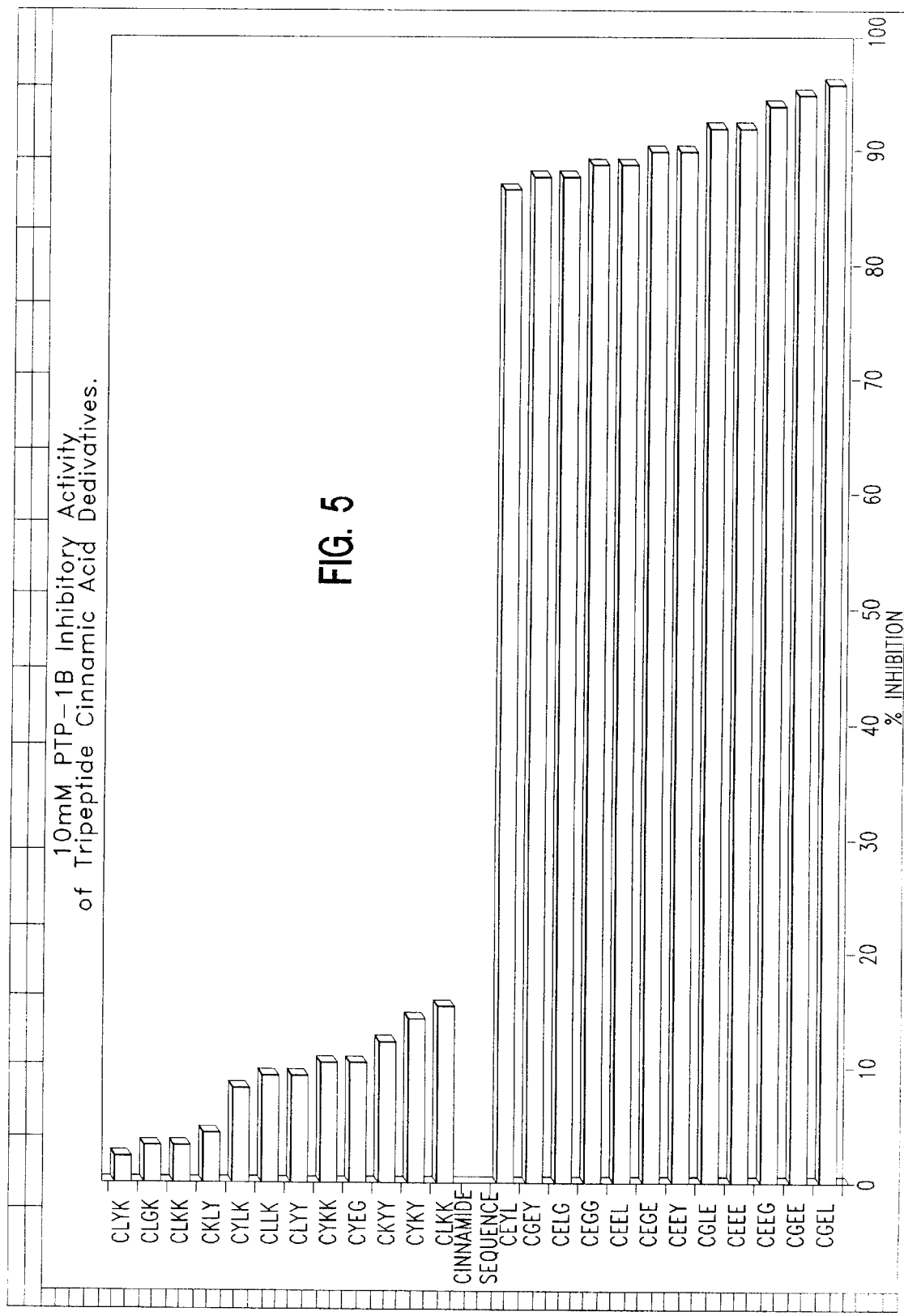

5,770,620

ARYL ACRYLIC ACID DERIVATIVES USEFUL AS PROTEIN TYROSINE PHOSPHATASE INHIBITORS

This application claims the benefit of the filing date of provisional application Ser. No. 60/107,610 filed Jun. 19, 1995.

FIELD OF THE INVENTION

The present invention provides novel protein tyrosine phosphatase modulating compounds, compositions comprising the compounds, and methods of making and using the same.

BACKGROUND OF THE INVENTION

Reversible phosphorylation and dephosphorylation of proteins comprises a prevalent biological mechanism for modulation of enzymatic activity in living organisms. Tonks et al, *J. Biol. Chem.*, 263(14):6722–30 (1988). Such reversible phosphorylation generally is thought to require both a protein kinase (PK), to phosphorylate a protein at a particular site, and a protein phosphatase (PP), to remove the phosphate moieties. See generally, Hunter, *Cell*, 80:225–236 (1995). Recently, it has been estimated that humans have as many as 2000 conventional PK genes, and as many as 1000 PP genes. Id.

One major class of PK's/PP's—the protein serine/threonine kinases/phosphatases—have been shown to play critical roles in the regulation of metabolism. See generally, Cohen, *Trends Biochem. Sci.*, 17:408–413 (1992); Shenolikar, *Ann. Rev. Cell Biol,* 10:55–86 (1994); Bollen et al., *Crit. Rev. Biochem. Mol. Biol.*, 27:227–81 (1992). As their name suggests, protein serine/threonine kinases and phosphatases phosphorylate and dephosphorylate serine or threonine moieties of substrate proteins. Inhibitors of protein serine/threonine phosphatases and kinases have been described. See, e.g., MacKintosh and MacKintosh, *TIBS,* 19:444–448 (1994).

The protein tyrosine kinases/phosphatases comprise a second, distinct family of PK/PP enzymes of significant interest, having been implicated in the control of normal and neoplastic cell growth and proliferation. See Fisher et al., *Science,* 253:401–406 (1991). Protein tyrosine kinase (PTK) genes are ancient in evolutionary origin and share a high degree of inter-species conservation. See generally Hunter and Cooper, *Ann. Rev. Biochem.,* 54:897–930 (1985). PTK enzymes exhibit high specificity for tyrosine, and ordinarily do not phosphorylate serine, threonine, or hydroxyproline.

Protein tyrosine phosphatases (PTPases) were originally identified and purified from cell and tissue lysates using a variety of artificial substrates, and therefore their natural function of dephosphorylation was not well characterized. Because tyrosine phosphorylation by PTK enzymes usually was associated with cell proliferation, cell transformation and cell differentiation, it was assumed that PTPases were also associated with these events. For a number of PTPases, this association has now been verified. For example, PTP-1B, the structure of which recently has been elucidated [Barford et al., *Science,* 263:1397–1404 (1994); Hoppe et al., *Eur. J. Biochem.,* 223:1069–77 (1994); Chernoff et al., *Proc. Natl. Acad. Sci USA,* 87:2735–39 (1990); Charbonneau et al., *Proc. Natl. Acad. Sci. USA,* 86:5252–5256 (1989)], has been shown to be involved in insulin-induced oocyte maturation. Cicirelli et al, *Proc. Nat'l Acad. Sci. USA,* 87:5514–18 (*1990*); Flint et al, *The EMBO J.,* 12:1937–46, (1993). The insulin-induced oocyte maturation mechanism has been correlated with the ability of PTP-1B to block activation of S6 kinase.

Recently, Weiner et al., *J. Natl Cancer Inst.,* 86:372–8 (1994), demonstrated a significant correlation between PTP-1B overexpression and breast cancer, and more specifically a correlation between PTP-1B overexpression and overexpression of p185$^{c-erbB-2}$, a PTK that is overexpressed in one-third of human breast cancer patients. A similar correlation has been demonstrated with respect to p185$^{c-erbB-2}$-associated ovarian cancers. Weiner et al., *Am J. Obstet. Gynecol.,* 170:1177–883 (1994).

Perhaps the best characterized PTPase molecule is the leukocyte-common antigen CD45. CD45, expressed exclusively on hemopoietic cells, is one of the most abundant of the cell surface glycoproteins and functions as a critical component in lymphocyte signal transduction. See generally Trowbridge and Thomas, *Ann. Rev. Immunol.,* 12:85–116 (1994). In particular, evidence suggests that CD45 plays a pivotal role in antigen-stimulated proliferation of both T and B lymphocytes. Trowbridge and Thomas, supra; Kishihara et al., *Cell,* 74:143–56 (1993). In a study employing CD45-deficient mice, CD45 was shown to be essential for the antibody-(IgE-) mediated degranulation of mast cells. Berger et al., *J. Exp. Med.,* 180:471–6 (1994).

A recently discovered, inducible lymphoid-specific protein tyrosine phosphatase designated HePTP has also been implicated in the immune response. HePTP is expressed in both resting T and B lymphocytes, but not non-hemopoietic cells. Upon stimulation of these cells, HePTP mRNA levels increase 10–15 fold. Zanke et al., *Eur. J. Immunol.,* 22:235–239 (1992).

The activity of a number of other newly discussed phosphatases are currently under investigation. Two of these: PTP-1C and Syp/PTP1D/SHPTP2/PTP2C have recently been implicated in the activation of Platelet Derived Growth Factor and Epidermal Growth Factor induced responses. Li et al., *Mol. Cell Biol.,* 14:509–17 (1994). Both of these growth factors are implicated in normal cell processing as well as disease states such as cancer and atherosclerosis, suggesting a therapeutic indication for inhibitors of these PTPase enzymes.

More generally, PTPases appear to be required for the mitogenic effects of certain cytokines (e.g., IL-4) and interferons. See Burke et al., *Biochem and Biophys Res. Comm.,* 204(1):129–34 (1994).

More than 40 members of the PTPase family have been identified in eukaryotes, prokaryotes, and even viruses. Barford et al., supra. Notably, the PTPase Yop2b is an essential virulence determinant in the pathogenic bacterium Yersinia, responsible for bubonic plague. Bliska et al., *Proc. Natl. Acad Sci. USA,* 88:1187–91 (1991).

A comparison of seven distinct transmembrane forms of protein tyrosine phosphatases (PTP) revealed that the extracellular segments of these proteins were quite diverse. In contrast, the intracellular segments shared striking similarities, including two conserved catalytic domains containing an essential cysteinyl residue (except HPTPβ, which has only one such catalytic domain). Fisher et al., supra; see also Barford et al., supra. The variable non-catalytic segments of PTPase proteins appear to control PTPase function, either by targeting of the PTPase molecule to specific subcellular compartments or through direct modulation of enzymatic activity. Flint et al., *The EMBO J.,* 12:1937–46, (1993).

Due to the fundamental role that PTPases are believed to play in normal and neoplastic cellular growth and proliferation, a need exists in the art for agents capable of modulating PTPase activity. On a fundamental level, such agents are useful for elucidating the precise role of protein tyrosine phosphatases and kinases in cellular signalling pathways and cellular growth and proliferation. See generally MacKintosh and MacKintosh, *TIBS*, 19:444–448 (1994).

More importantly, modulation of PTPase activity has important clinical significance. For example, because overexpression of PTP-1B has been correlated with neoplastic conditions, agents which modulate PTP-1B activity are needed for clarifying the role of PTP-1B in these conditions and for development of effective therapeutics against these disease states. The important role of CD45 in hematopoietic development likewise indicates a therapeutic utility for PTPase inhibitors in conditions that are associated with autoimmune disease. The role of CD45 in antibody-mediated degranulation of mast cells indicates a therapeutic utility of PTPase inhibitors for allergic disorders. Similarly, the role of HePTP in immune response indicates a therapeutic utility for HePTP inhibitors in diseases associated with the immune system.

Because a PTPase protein is essential to the virulence of pathogenic Yersinia strains, an antibiotic indication exists for PTPase inhibitor compounds, too. The antibiotic suramin, which also appears to possess anti-neoplastic indications, has recently been shown to be a potent, irreversible, non-competitive inhibitor of CD45. See Ghosh and Miller, *Biochem. Biophys. Res. Comm.* 194:36–44 (1993).

PTPases have been implicated in diabetic conditions. Experiments with one family of PTPase inhibitors, vanadium derivatives, indicate a therapeutic utility for such compounds as oral adjuvants or as alternatives to insulin for the treatment of hyperglycemia. See Posner et al., *J. Biol. Chem.*, 269:4596–4604 (1994). However, such metal-containing PTPase inhibitors would be expected to act in a fairly non-specific fashion (Burke et al., supra) and act with similar potencies against all PTPase enzymes.

In addition to vanadium derivatives, certain organic phosphotyrosine mimetics are reportedly capable of competitively inhibiting PTPase molecules when such mimetics are incorporated into polypeptide artificial PTPase substrates of 6–11 amino acid residues. For example, a "natural" (phosphorylated tyrosine) PTPase substrate, which may be depicted by the formula

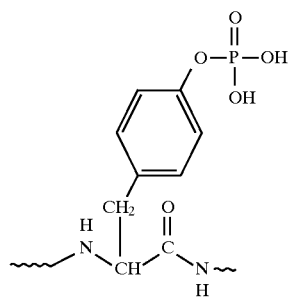

has been mimicked by eleven-mer oligopeptides containing phosphonomethyl phenylalanine (Pmp), as depicted by the schematic formula

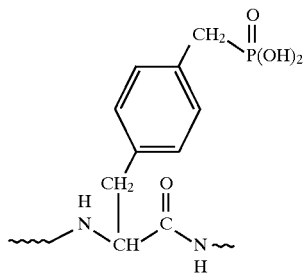

See Chatterjee et al, "Phosphopeptide substrates and phosphonopeptide inhibitors of protein tyrosine phosphatases," in *Peptides: Chemistry and Biology* (Rivier and Smith, Eds.), 1992, Escom Science Publishers: Leiden, Netherlands, pp. 553–55; Burke et al, *Biochemistry*, 33:6490–94 (1994). More recently, Burke et al., *Biochem. Biophys. Res. Comm.* 204(1):129–134 (1994) reported that a particular hexameric peptide sequence comprising a Pmp moiety or, more preferably, a phosphonodifluoromethylphenylalanine ($F_2$Pmp) moiety, as depicted by the schematic formula

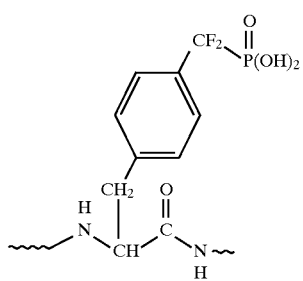

competitively inhibited PTP-1B. However, such hexapeptide inhibitors nonetheless possess drawbacks for PTPase modulation in vivo. More particularly, the hexapeptide inhibitors described by Burke et al. are sufficiently large and anionic to potentially inhibit efficient migration across cell membranes, for interaction with the catalytic domains of transmembrane and intracellular PTPase enzymes which lie within a cell membrane. A need exists for small, organic-molecule based PTPase inhibitors having fewer anionic moieties, to facilitate migration across cell membranes.

For all of the foregoing reasons, a need exists in the art for novel compounds effective for modulating, and especially inhibiting, the phosphatase activity of protein tyrosine phosphatase molecules.

SUMMARY OF THE INVENTION

The invention provides aryl acrylic acid compounds and derivatives thereof useful for modulating, and especially inhibiting, the phosphatase activity of one or more protein tyrosine phosphatase (PTPase) enzymes such as PTP-1B and/or HePTP. The inventions further provides salts, esters, solvates, and the like of the compounds, and compositions comprising the compounds.

The present invention is based on the discovery that aryl acrylic acid compounds of the formula (A) below and their derivatives inhibit protein tyrosine phosphatase activity:

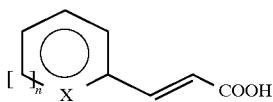

(A)

wherein n=0 or 1, and when n=1, X is CH or Nitrogen (i.e., the aryl group is a phenyl or pyridyl group, respectively), and when n=0, X is oxygen or sulfur (i.e., the aryl group is a furyl or thiophenyl (thienyl) group, respectively).

By "derivatives" is meant: aryl acrylic acids of formula (A) having substitution (with, e.g., hydroxy, halo, amino, carboxy, nitro, cyano, methoxy, etc.) at one or more atoms of the aromatic ring, as set forth in greater detail below, in Table 4, and in Example 11. Moreover, "derivatives" includes compounds of the formula (A) having substitution at the alkene carbons with, e.g., an electron withdrawing group (e.g., Cl, F, Br, $CF_3$, phenyl) or an electron donating group (e.g., $CH_3$, alkoxy); and compounds of formula (A) wherein the carboxylic acid group is replaced with, e.g., a tetrazolyl group, or esterified with, e.g., an imidazole.

In one aspect, the invention includes protein tyrosine phosphatase modulating compounds having the formula (AA):

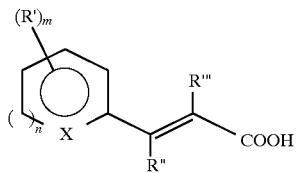

(AA)

(a) wherein n=0 or 1,
  (i) when n=1, X is selected from the group consisting of N and CH, and
  (ii) when n=0, X is selected from the group consisting of O and S;
(b) wherein m is an integer from 0 to 4 and each R' is independently selected from the group consisting of halo, nitro, amino, hydroxy, carboxy, $C_{1-11}$ alkyl, carboxy $C_{1-6}$ alkyl, —CH=CHCOOH, $C_{1-6}$ alkyloxy, trihalomethyl, formyl, $C_{1-6}$ alkylcarbonyl, and hydroxy $C_{1-6}$ alkyl; and
(c) wherein R" and R'" are independently selected from the group consisting of hydrogen, halo, cyano, phenyl, and $C_{1-11}$ alkyl. Preferred compositions of the invention include compositions comprising such compounds (or pharmaceutically acceptable salts, esters, or solvates of the compounds) in admixture with a pharmaceutically acceptable diluent, adjuvent, or carrier.

Preferred protein tyrosine phosphatase activity-modulating aryl acrylic acid derivative compounds according to the invention have the following general structural formula (I):

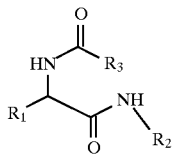

(I)

(a) wherein at least one of $R_1$, $R_2$ and $R_3$ substituents has the formula (IR)

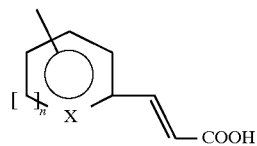

(IR)

wherein n=0 or 1, X is selected from the group consisting of N and CH when n=1, and X is selected from the group consisting of O and S when n=0; and (b) wherein the remaining of $R_1$, $R_2$ and $R_3$ are independently selected from the group consisting of
  (i) hydrogen, $C_{1-11}$ alkyl,
  (ii) substituted $C_{1-11}$ alkyl, wherein the substituent is selected from the group consisting of hydroxy, halo, mercapto, amino, carboxy, carbamoyl, guanidino, aryl, hydroxyphenyl, $C_{1-6}$ alkyloxy, $C_{1-6}$ alkylthio, $C_{1-6}$ alkylamino, phenyl $C_{1-6}$ alkyloxy, phenyl $C_{1-6}$ alkylthio and phenyl $C_{1-6}$ alkylamino;
  (iii) aryl,
  (iv) $C_{1-11}$ alkyl aryl;
  (v) mono-, di- and tri-substituted aryl, wherein the substituents are independently selected from $C_{1-6}$ alkyl, trifluoromethyl, hydroxy, halo, $C_{1-6}$ alkyloxy, $C_{1-6}$ alkylthio, amino, $C_{1-6}$ alkylamino, amino $C_{1-6}$ alkyl, $C_{1-6}$ alkylcarbonyl, $C_{1-6}$ alkylcarbonylamino, $C_{1-6}$ alkylaminocarbonyl, carboxy, and carboxy $C_{1-6}$ alkyl; and
  (vi) $CH_2COX'R_4$, wherein X' is oxygen or NH and $R_4$ is independently selected from hydrogen, $C_1$–$C_{11}$ alkyl, aryl, and $C_1$–$C_{11}$ alkyl aryl;

wherein the aryl of (ii), (iii), (iv), (v), and (vi) are independently selected from the group consisting of phenyl, naphthyl, pyridyl, furyl, pyrryl, thienyl, isothiazolyl, imidazolyl, benzimidazolyl, tetrazolyl, pyrazinyl, pyrimidyl, quinolyl, isoquinolyl, benzofuryl, benzothienyl, pyrazolyl, indolyl, benzodioxolyl, piperonyl, isoindolyl, purinyl, carbazolyl, isoxazolyl, thiazolyl, oxazolyl, benzthiazolyl, and benzoxazolyl; and (c) wherein when $R_3$ of Formula (I) has the formula (IR), $R_2$ may further be of the formula (B)

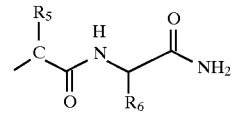

(B)

wherein $R_5$ and $R_6$ are independently selected from the group consisting of (b) (i) and (b) (ii).

In preferred embodiments, $R_3$ of Formula (I) has the formula

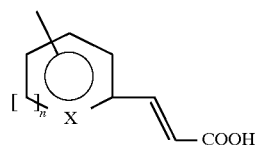

wherein n and X are defined as above for Formula (IR). In particularly preferred embodiments $R_3$ is a cinnamic acid substituent, that is, n=1 and X=CH. These compounds therefore are of the general Formula (II)

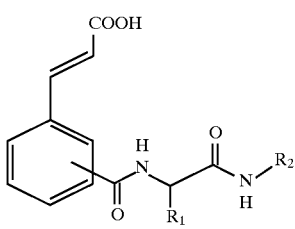

(II)

wherein $R_1$ and $R_2$ are defined as above with respect to compounds of Formula (I).

It is preferred that the PTPase modulating compounds of Formula (II) are para- substituted cinnamic acid derivative compounds of the general formula (IIA)

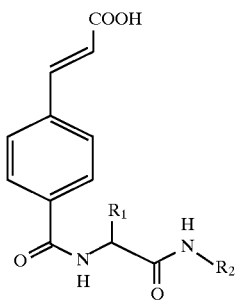

(IIA)

wherein $R_1$ and $R_2$ are defined as described above.

As used herein, the term "alkyl" includes branched or straight chain and cyclic (e.g., cycloalkyl) saturated aliphatic hydrocarbon groups having the specified number of carbon atoms, e.g., methyl (Me), ethyl (Et), propyl (Pr), butyl (Bu), pentyl, hexyl, heptyl, octyl, nonyl, decyl, isopropyl (i-Pr), isobutyl (i-Bu), tert-butyl (t-Bu), sec-butyl (s-Bu), isopentyl, cyclohexyl, and the like.

The terms "alkyloxy" or "alkoxy" represent an alkyl group as defined above having the indicated number of carbon atoms attached through an oxygen bridge, e.g., methoxy, ethoxy, propyloxy, and the like.

The terms "alkylthio" and "alkylamino" represent an alkyl group as defined above having the indicated number of carbon atoms attached through a sulfur bridge or an amine bridge, respectively. The amine bridge may itself be substituted with an alkyl or aryl group. Similarly, the term "amino" is intended to include alkyl substituted amino groups.

The term "amino alkyl" (e.g., "amino $C_{1-6}$ alkyl") represents an amino group as defined above attached through an alkyl group as defined above having the indicated number of carbon atoms, the amino group being attached to any carbon of the alkyl group.

The term "alkylcarbonyl" represents an alkyl group as defined above having the indicated number of carbon atoms attached through a carbonyl group. The term "alkylcarbonylamino" represents an alkylcarbonyl group as defined above wherein the carbonyl is in turn attached through the nitrogen atom of an amino group as defined above.

The term "alkylaminocarbonyl" represents an alkyl group as defined above having the indicated number of carbon atoms attached through the nitrogen atom of an amino group as defined above, the nitrogen atom in turn being attached through a carbonyl group.

The term "carboxy alkyl" (e.g., "carboxy $C_{1-6}$ alkyl") represents a carboxy group attached through an alkyl group as defined above having the indicated number of carbon atoms, the carboxy group being attached to any carbon of the alkyl group.

The term "aryl" includes the indicated monocyclic polycyclic, and heterocyclic aromatic groups covalently attached at any ring position capable of forming a stable covalent bond with the aryl group, certain preferred points of attachment being apparent to those skilled in the art (e.g., 3-indolyl, 4-imidazolyl).

The term "alkyl aryl" represents an alkyl group as defined above having the indicated number of carbon atoms attached through an aryl group as defined above, the alkyl group being attached at any position of the aryl group capable of forming a stable covalent bond with the alkyl group.

The term "phenyl alkyl" (e.g., "phenyl $C_{1-6}$ alkyloxy," "phenyl $C_{1-6}$ alkylthio," "phenyl $C_{1-6}$ alkylamino") represents a phenyl group attached through an alkyl group as defined above having the indicated number of carbon atoms, the phenyl group being attached to any carbon of the alkyl group (the alkyl group in turn attached through an oxygen bridge, a sulfur bridge, an amine bridge, etc.).

Preferred protein tyrosine phosphatase activity modulating/inhibiting compounds of the invention are carboxyl substituted cinnamic acids wherein the carboxyl group ring substituent is derivatized to form an amide. In some presently preferred forms of these compounds, the amide linkage joins the carboxyl-substituted cinnamic acid moiety to a dipeptide or tripeptide moiety structurally resembling or identical to a dipeptide or tripeptide of naturally-occurring amino acids.

Provided according to the invention, therefore, are novel aryl acrylic acid compounds having phosphatase modulating activity as well as new phosphatase activity modulating uses for previously known aryl acrylic acid compounds.

Another aspect of the present invention provides compositions comprising PTPase modulating compounds of the invention suitable for administration to a mammalian host.

The invention further provides methods for making compounds of the present invention having PTPase-modulatory/inhibitory activity. In preferred methods, compounds of the invention are synthesized in a multi-component combinatorial array, which permits rapid synthesis of numerous, structurally related compounds for subsequent evaluation. In preferred synthesis protocols, the acrylic acid moiety of a compound is protected during synthesis by, e.g., esterification with a t-butyl protecting group. Thus, a preferred method of making compounds of the invention comprises use of a protected acrylic acid reagent and removal of the protective group by, e.g., treatment of a precursor ester compound with acid. Optionally, such a method includes further esterifying or salifying the acrylic acid product thereby obtained.

Numerous other aspects and advantages of the present invention will be apparent upon the following detailed description thereof, reference being made to the drawing wherein:

FIG. 3 depicts the synthesis of aryl acrylate reagents, which reagents were utilized to synthesize PTPase activity-modulating compounds of the invention.

FIG. 5 depicts the inhibitory activity, expressed as % inhibition at 10 mM concentrations, of tripeptide amide cinnamic acid derivatives of the invention. Individual tripeptide amide compounds are depicted by the letter C (for p-carboxycinnamate) followed by a three-letter tri-peptide designation.

DETAILED DESCRIPTION

Figure 1:
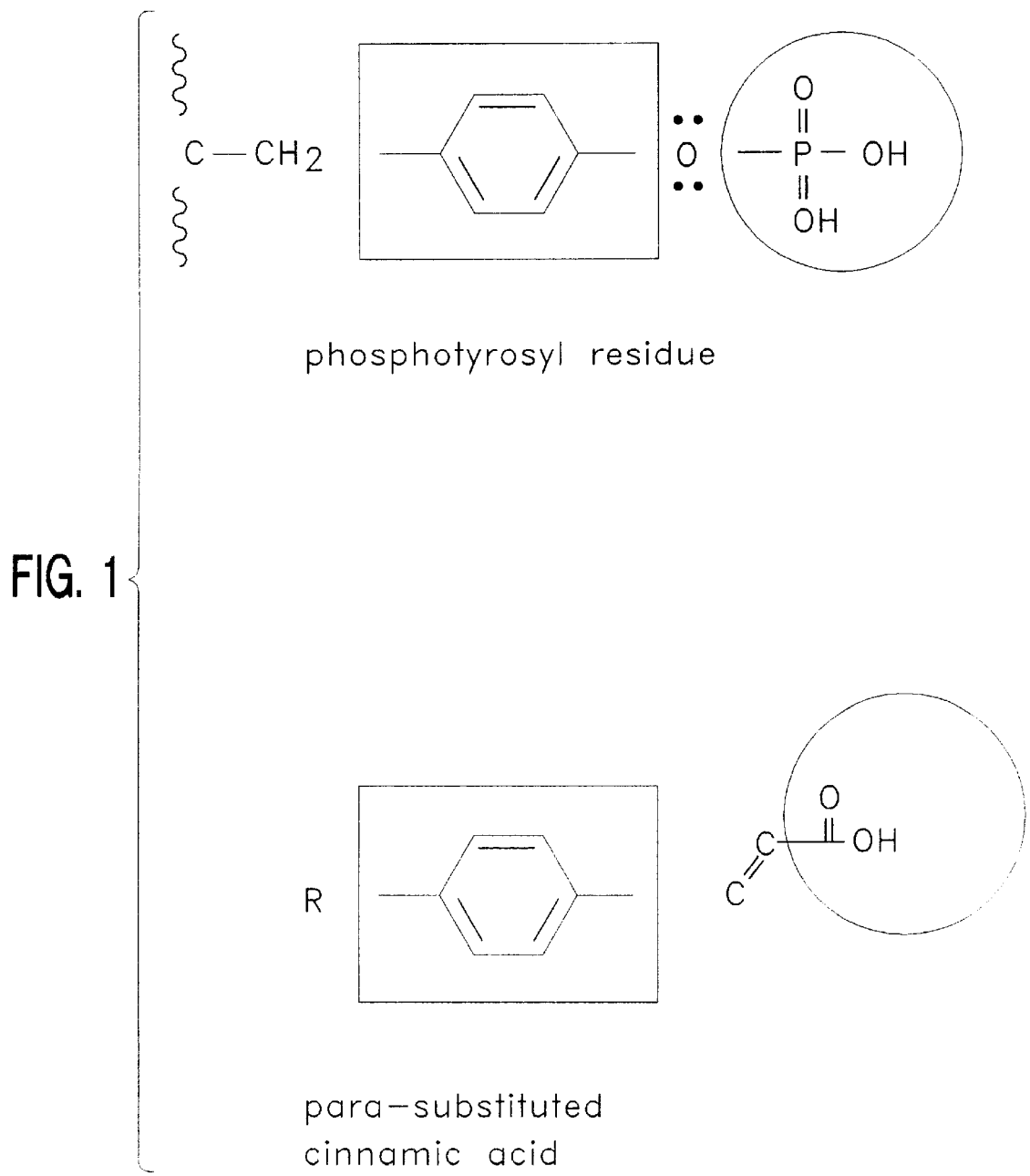
FIG. 1 depicts a phosphotyrosyl structure and a cinnamic acid derivative structure according to the present invention.

Without intending to be limited to a particular theory, it is believed that the PTPase inhibitory activity of substituted and unsubstituted acrylic acids, aryl acrylic acids, and derivatized aryl acrylic acids is attributable to subtle steric and electronic similarities between the aryl acrylic acid moiety of such compounds and a phosphorylated tyrosine (phosphotyrosyl) moiety that is the natural target of PTPase enzymes. As depicted in FIG. 1, a phosphotyrosyl residue has a phenyl component (boxed) covalently linked to a phosphono component (circled) through an oxygen atom. This oxygen atom is believed to be a locus of chemical interaction between a phosphotyrosyl residue and the catalytic domain(s) of a protein tyrosine phosphatase enzyme. In comparison, an aryl acrylic acid derivative, such as para-substituted cinnamic acid, has a phenyl component (boxed) covalently linked to a carboxylic acid component (circled) through an alkene group. It is believed that the phosphono and corresponding carboxylic acid component, the corresponding aromatic components, and the oxygen and corresponding alkene components of these moieties depicted in FIG. 1 possess sufficient steric and electronic similarity for the aryl acrylic acid moiety to compete with the phosphotyrosyl moiety for binding to the catalytic domain of PTPase enzymes, thereby inhibiting PTPase activity of such enzymes.

The steric requirements of aryl acrylic acid PTPase inhibitors according to the invention were further characterized by assaying derivatives of such molecules for PTPase activity. Importantly, it was determined that esterification of the carboxylic acid, and/or reduction of the alkene bond, substantially eliminates PTPase inhibitory activity of these compounds. Equally importantly, it was determined that a measure of variability is permissible with respect to the aryl substituent of the PTPase inhibitors of the invention. Thus, in addition to para-substituted phenyl acrylic acids (cinnamic acids), which most closely resemble the structure of a phosphotyrosyl residue, it has been determined that ortho- and meta- substituted cinnamic acids inhibit PTPase activity. It has further been determined that unsubstituted and substituted furylacrylic acid, pyridylacrylic acid, thienylacrylic acid, and other acrylic acids inhibit PTPase enzymatic activity; and that aryl acrylic acids having substitution at the alkene carbons or substitution at more than one atom of the aromatic ring inhibit PTPase enzymatic activity.

Any method may be used to synthesize compounds of the invention, and it is contemplated that conventional organic chemical syntheses may be employed to produce compounds of the invention on a commercial scale. However, in a preferred method, PTPase compounds of formula (I) are synthesized using a four-component combinatorial array Ugi Reaction synthesis as described in International Patent Application No. PCT/US94/08141, filed Jul. 15, 1994 and published Jan. 26, 1995 (Publication No. WO 95/02566). See also Ugi et al., "Multicomponent Reactions In Organic Chemistry," in *Endeavor, New Series*, Vol. 18, No. 3, Elsevier Science Ltd., Great Britain (1994).

Each component in the multicomponent synthesis comprises a series of reagent compounds sharing one or more common functional groups, e.g., an amine, an aldehyde, etc. The synthesis is conducted under conditions such that the common functional groups of the compounds of the various components react with one another to form product compounds having a common core structure. More particularly, the series of reagents that comprise each individual component are added to a plurality of reaction vessels "combinatorially" to form an array, such that each reaction vessel of the array contains a unique combination of individual reagents. The reagent components are added under appropriate conditions such that a unique product, sharing the common core structure of interest, forms in each reaction vessel. The total number of analogs synthesized is equal to the product of the number of structural variants of each component in the array. Thus, the multicomponent combinatorial array synthesis provides a relatively simple and rapid means for synthesis of a library of numerous structural variants sharing a core structure of interest.

Figure 2:
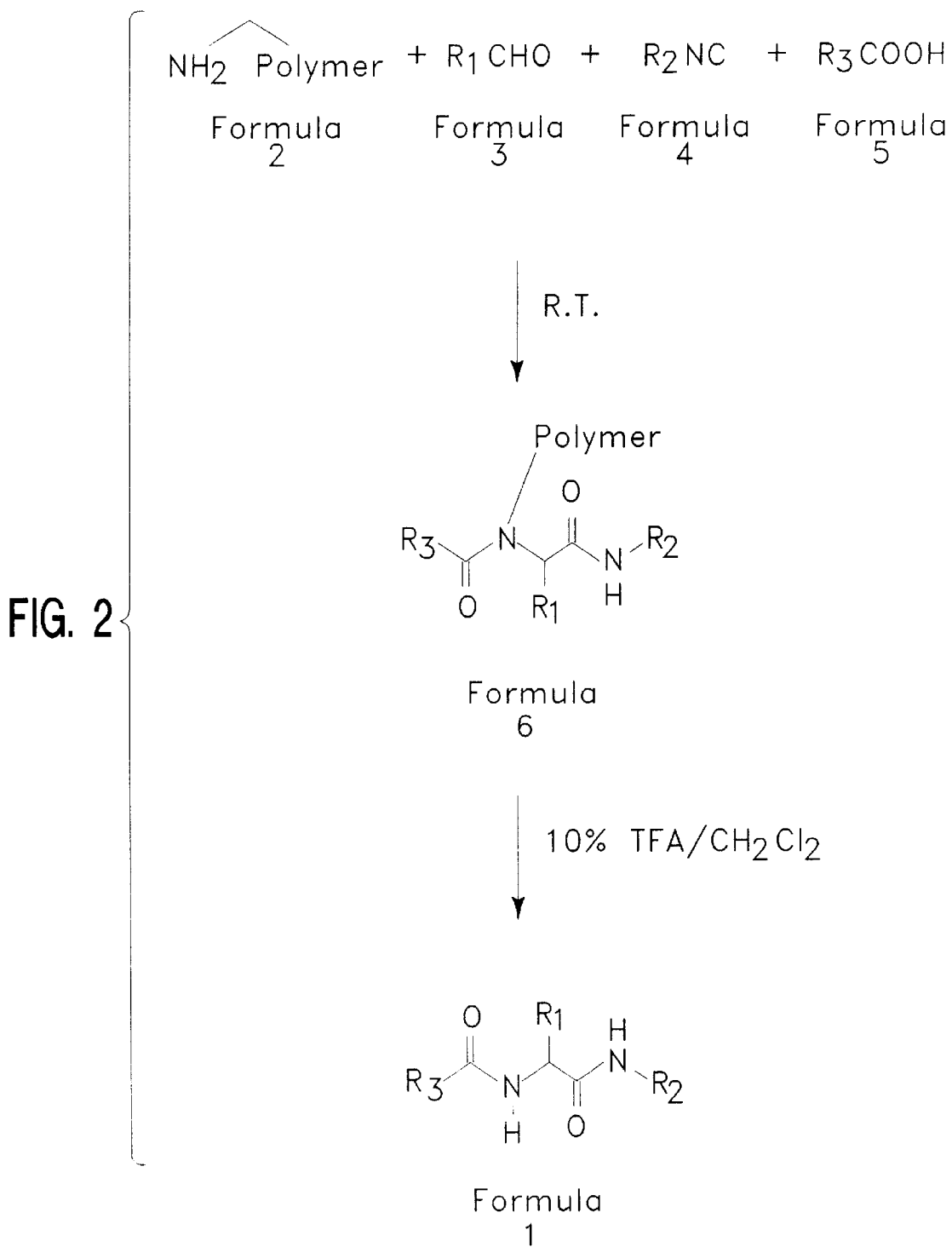
FIG. 2 depicts the four-component Ugi Reaction synthesis of compounds of the present invention.

More particularly, to synthesize compounds of formula (1), an Ugi Reaction as depicted in FIG. 2 is conducted, wherein the four reagent components of a given reaction are (a) an aldehyde of formula 3; (b) a commercially available Rink resin or other suitable solid support resin of formula 2; (c) an isocyanide of formula 4; and (d) an acid of formula 5. In a first stage, the four components are reacted to yield a compound of formula 6. In a second stage, the compound of Formula 6 is reacted with an acid, e.g., 10% trifluoroacetic acid (TFA) in $CH_2Cl_2$, to yield a compound of formula (I). Optionally, the compound is then esterified, salified, or otherwise formulated to form compositions as described herein.

In addition to providing methods for synthesis of the compounds herein described, the invention provides in vitro procedures for screening the compounds for PTPase inhibitory activity. The preferred screening procedure is rapid and can be performed with micromolar quantities of the compounds of interest. Thus, according to the present invention large numbers of compounds can be synthesized rapidly and inexpensively on a very small scale, and subjected to a rapid initial screening, followed by a full-scale screening, to select protein tyrosine phophatase-modulating compounds of particular interest.

Moreover, although the PTPase inhibition assays are described herein with respect to two particular PTPase molecules (PTP-1B and HePTP), it is understood that numerous additional PTPase enzymes have been characterized, and that other PTPase molecules are expected to be identified and characterized. The assays described herein and other in vitro and in vivo PTPase inhibition assays may be conducted with such other enzymes, to demonstrate the PTPase modulating properties of compounds of the invention.

The following examples further illustrate aspects of the invention. In Example 1, the synthesis of aryl acrylate reagents is described, which reagents are useful for Ugi Reaction synthesis of compounds of the invention. In Example 2, the use of such aryl acrylate reagents to synthesize cinnamic acid derivative compounds of the invention is described.

Examples 3 through 5 pertain to protocols for assaying compounds of the invention for PTPase modulating activity. In particular, Example 3 describes the purification of a truncated PTP-1B fusion protein possessing PTPase activity, which fusion protein was employed to assay PTPase inhibitory activity of compounds of the invention. Example 4 describes the purification of a second recombinant PTPase enzyme, HePTP, which also was employed to assay the PTPase modulating activity of compounds of the invention. Example 5 describes with particularity the PTPase inhibition assays conducted with PTP-1B and HePTP.

Examples 6 through 8 describe the synthesis and characterization of additional cinnamic acid derivative compounds of the invention. Example 9 describes the synthesis and characterization of a number of furylacrylic acid derivative compounds of the invention.

Example 10 describes a procedure whereby the PTPase inhibitory activity of a variety of commercially available aryl acrylic acids was demonstrated.

Example 11 describes a library of 125 cinnamic acid derivative compounds synthesized using known protocols. The library comprises a family of cinnamic acid derivatives having tripeptide amide substituents of considerable functional variation. As taught in Example 10, small compound libraries designed in this manner and screened for PTPase modulating activity against a selected enzyme provide useful information for designing PTPase modulating compounds with enhanced activity against the selected enzyme.

Example 12 describes a whole cell growth-inhibition assay in which compounds of the invention demonstrated cell growth inhibitory activity.

EXAMPLE 1

Synthesis of Aryl Acrylate Reagents

In preferred embodiments described above, compounds of formula (1) are synthesized using an Ugi reaction synthesis (see FIG. 2), wherein $R_3$ of formula (I) has the formula:

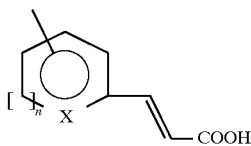

wherein n and X are defined as described above for formula (IR). To synthesize such PTPase inhibiting compounds using the Ugi Reaction, the $R_3$ substituent was provided using aryl acrylate reagents, which reagents were synthesized as follows.

Referring to FIG. 3, a mixture of approx. 10 mmol of an aryl bromide compound of general formula (1), 12.5 mmol of t-butyl acrylate, 20 mmol of dry triethylamine, 0.1 mmol of palladium acetate, and 0.4 mmol of tri-o-tolylphosphine is prepared in a flask. The flask is blown out with argon and heated at 100° C. This reaction may be monitored using thin layer chromotography, which reveals that, after about 2 hours, all of the aryl bromide compound has reacted, forming a solid product. The solid product is extracted with EtOAc and water and then adjusted to pH 3 using 1N HCl. The organic phase is filtered, dried over sodium sulfate, and further dried by evaporation.

Where the initial aryl bromide reagent of formula (1) is a methyl ester (i.e., R=Me), then the reaction product of general formula (2) is hydrolized to the desired acid reagent of general formula (3), using 0.5M LiOH in a 1:1 mixture of 1,4-dioxane:water. The reagent of general formula (3) is dried and its identity confirmed by NMR and mass spectrometry. The dried reagent of general formula (3) is suitable for use in a carboxylic acid reagent in an Ugi Reaction synthesis as described herein. Exemplary NMR and mass spectrometry data is provided below for selected compounds:

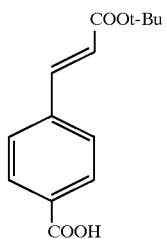

H-NMR(CDCl$_3$) δ: 1.46 ppm(s, 9H); 6.42 ppm(d, 1H); 7.56–7.59 ppm(m,3H); 8.12 ppm(d, 2H).
M.S. 248.3 (calculated); 247.0 (observed)

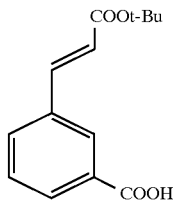

H-NMR(CDCl$_3$) δ: 1.45 ppm(s, 9H); 6.41 ppm(d, 1H); 7.41 ppm(t,1H); 7.58 ppm(d, 1H); 7.62ppm(d, 1H); 8.04ppm(d, 1H); 8.21 ppm(s, 1H).
M.S. 248.3 (calculated); 247.0 (observed).

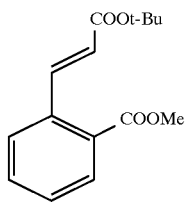

H-NMR(CDCl$_3$) δ: 1.45 ppm(s, 9H); 3.84 ppm(s, 3H); 6.19 ppm(d, 1H); 7.36 ppm(t, 1H); 7.43ppm(t, 1H); 7.52ppm(d, 1H); 7.86ppm(d, 1H); 8.24ppm(d, 2H).

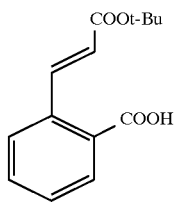

H-NMR(CDCl$_3$) δ: 1.45 ppm(s, 9H); 6.21 ppm(d, 1H); 7.42 ppm(t, 1H); 7.47 ppm(t, 1H); 7.50 ppm(d, 1H); 8.06 ppm(d, 1H); 8.42 ppm(d, 2H).
M.S. 248.3 (calc.), 247.0 (obs.)

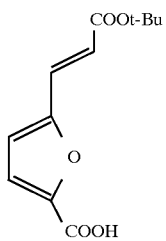

H-NMR(CDCl$_3$) δ: 1.46 ppm(s, 9H); 6.28 ppm(d, 1H); 7.03 ppm(d, 1H); 7.22 ppm(d, 1H); 7.33 ppm(d, 2H).

EXAMPLE 2

Cinnamic Acid Derivative Synthesis and Initial Screening for PTPase Inhibitory Activity Cinnamic acid derivative compounds were synthesized in a combinatorial Ugi Reaction and initially screened for protein tyrosine phosphatase modulating activity as set forth below.

Figure 4:
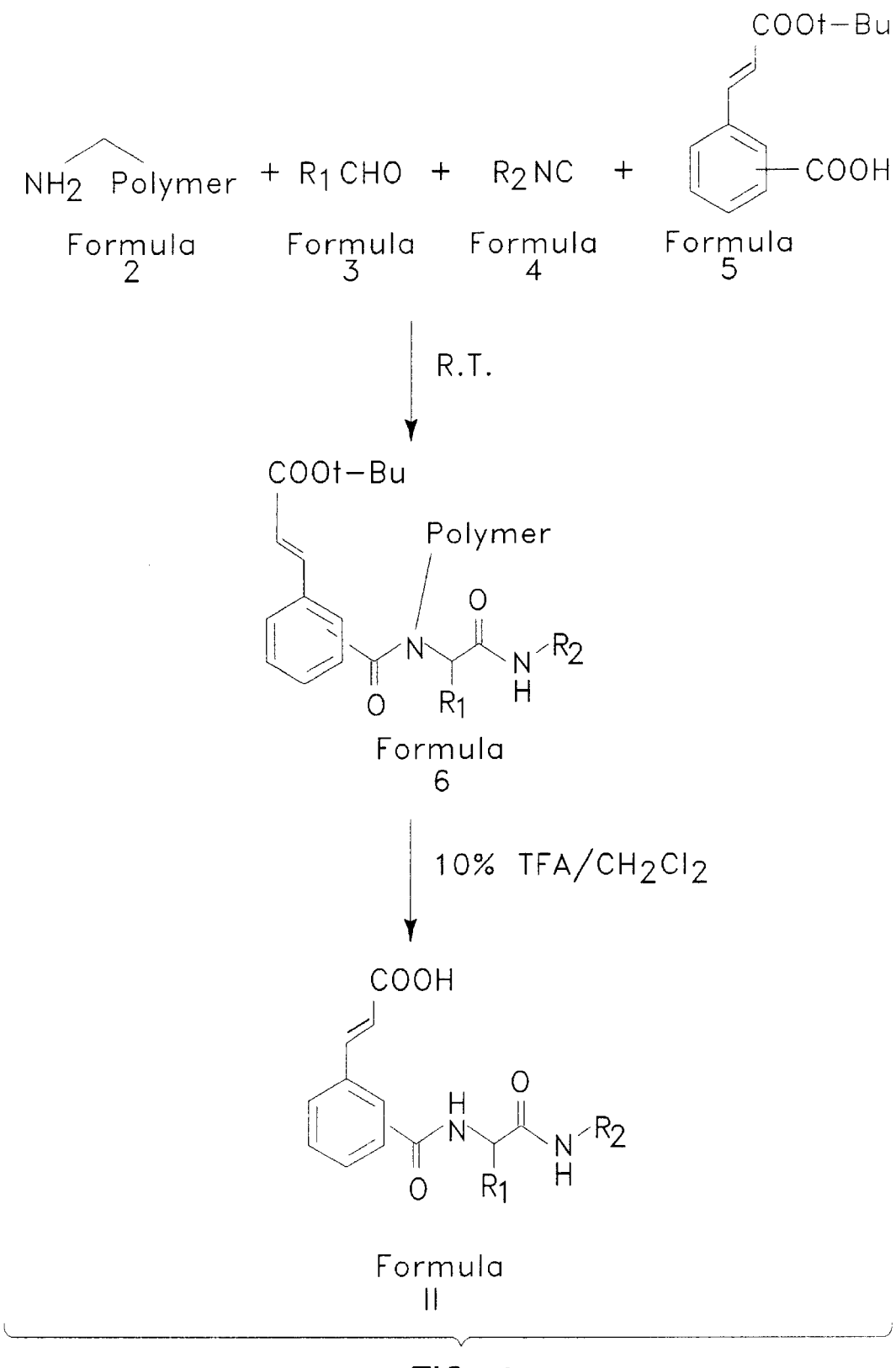
FIG. 4 depicts the four component Ugi Reaction synthesis of compounds of the present invention, wherein a carboxylic acid t-butyl cinnamate reagent is employed.

Referring to FIG. 4 herein, the four reagent components of a given reaction are (a) an aldehyde of formula 3; (b) a commercially available Rink resin of formula 2; (c) an isocyanide of formula 4; and (d) a cinnamic acid derivative of formula 5. In a first stage, the four components are reacted to yield a compound of Formula 6. In a second stage, the compound of Formula 6 is reacted with 10% trifluoroacetic acid (TFA) in $CH_2Cl_2$ to yield a compound of Formula II.

More particularly, a 0.5M solution of each component is prepared, e.g., by dissolving 0.05 mMoles of the component in 100 µl of an appropriate preferred solvent set as forth in Table 1:

TABLE 1

| Component | Solvent |
|---|---|
| Aldehyde | MeOH or $CH_2Cl_2$ |
| Rink Resin | MeOH |
| Isocyanide | MeOH |
| Acid | MeOH or DMSO |

Other appropriate solvents (e.g., acetonitrile, THF, chloroform) will be apparent to those of ordinary skill. Commercially available aldehyde compounds of Formula 3 were selected to provide $R_1$=methyl, ethyl, n-propyl, n-butyl, n-hexyl, n-heptyl, phenyl, and $PhCH_2CH_2$. Commercially available isocyanide compounds of Formula 4 were selected to provide $R_2$=n-butyl; 1,1,3,3-tetramethylbutyl; t-butyl; $CH_2CO_2H$; $CH_2CO_2Methyl$; $CH_2CO_2Ethyl$; cyclohexyl; and benzyl. Ortho-, meta-, and para- carboxylic acid t-butyl cinnamate was synthesized as described in the previous example to provide the acid reagents of Formula 5.

The multi-component combinatorial synthesis reactions were performed using Ontogen (Carlsbad, Calif.) 96-well reaction plates (2.0 ml/well capacity) and the multisynthesizer described in co-owned, co-pending U.S. patent application Ser. No. 08/422,869 (Attorney Docket No. 8140-008-999), filed Apr. 18, 1995 (John Cargill and Romaine R. Maiefsky, inventors) entitled "Methods and Apparatus for the Generation of Chemical Libraries."

First, a solution of the Rink resin (4-(2',4'-Dimethoxyphenyl-Fmoc-aminomethyl)-phenoxy Resin, Advanced ChemTech (ACT, Louisville, Ky.)), which provides an amine linkage group, was distributed across each plate into 80 wells, in an 8×10 array (100 µl/well). Solutions of the aldehyde compounds were then added across each plate in combinatorial fashion (100 µl/well). The plates were placed on the orbital shaker for one hour at room temperature.

Thereafter, the plates were again placed on the multisynthesizer, and the acid and isocyanide solutions were added across the plates in essentially combinatorial fashion. Distribution of aldehydes, isocyanides, and acids in "combinatorial fashion" involves distribution of distinct aldehydes (e.g., having different $R_1$ groups), distinct isocyanides (e.g., having different $R_2$ groups) and distinct acids (e.g., ortho-, meta-, or para- substituted) in a three-dimensional array on a series of plates, such that a unique compound is synthesized in each well of each plate. For example, eight distinct aldehydes, ten distinct isocyanides, and three distinct acid components may be combined combinatorially on three plates (80 wells/plate) to produce at least 240 distinct compounds (ignoring, e.g., stereochemistry) within the genus of Formula II.

After combinatorial addition of the acid and isocyanide solutions to the wells, the plates were placed on an orbital shaker for 72 hours at room temperature. It will be apparent that the synthesis reactions may be conducted at higher temperatures (e.g., up to about 80°–90° C.), limited essentially by the boiling point of selected solvents or of reagents. Thereafter, the solvent in the plates was drained and the resin was washed three times with DMSO and then three times dichloromethane (DCM). At this stage of the synthesis, each well contains a compound covalently linked to the rink resin as depicted in Formula 6 (FIG. 4).

To obtain the compounds of the present invention, the Rink resin polymer and t-butyl protective group were removed by treatment with dry acid. A solution of 10% trifluoroacetic acid (TFA) in DCM (600 ul) was added to each well and the plates were shaken for twenty minutes on the orbital shaker. The solvent in the wells (in which the compounds of interest were dissolved) was then drained and the wells were rinsed again with the TFA solution (300 ul). The TFA solution was then removed by evaporation in a vacuum oven to provide one compound of Formula II per reaction (approx. 0.025 mmol compound per reaction).

The reaction products from the combinatorial synthesis were resuspended in DMSO and screened for PTPase inhibitory activity using the in vitro PTPase inhibition assays described in Example 5, below. More particularly, based on an assumption that each synthesis yielded approximately 0.025 mmol of the desired reaction product, the compounds were screened for PTP-1B or HePTP inhibitory activity at an effective concentration of 10 µM. Compounds exhibiting at least about 50 percent inhibition against at least one of these enzymes were selected for further analysis.

Compounds selected for further analysis were resynthesized in the same manner described above and their identity and purity was confirmed by mass spectrometry and nuclear magnetic resonance spectroscopy (NMR). Exemplary NMR and mass spectrometry data for selected compounds is set forth below.

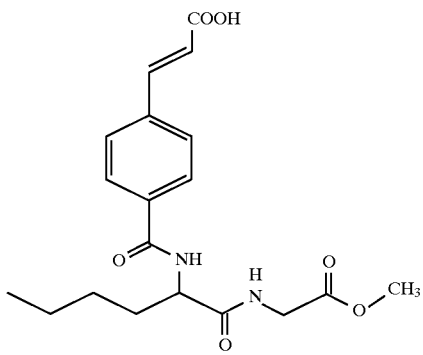

$^1$HNMR (CDCl$_3$): δ0.86 (t, 3H); 1.22–1.46 (m, 4H); 1.84–1.95 (m, 2H); 3.76 (s, 3H); 4.05 (m, 2H); 4.74 (m, 1H); 6.63 (d, 1H); 7.04–7.43 (m, 5H).

M.S. 376.2(calc.): 375.0(obs.)

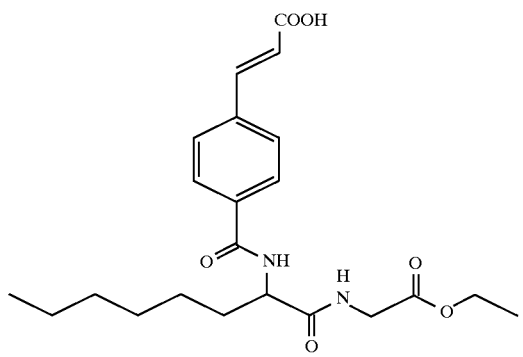

¹HNMR (CD₃OD): δ0.84 (t, 3H); 1.22 (t, 3H); 1.30–1.46 (m, 8H); 1.73–1.95 (m, 2H); 3.90 (q, 2H); 4.12 (q, 2H); 4.56 (t, 1H); 6.56 (d, 1H); 7.64–7.93 (m, 5H).
M.S. 418.2(calc.); 417.0(obs.).

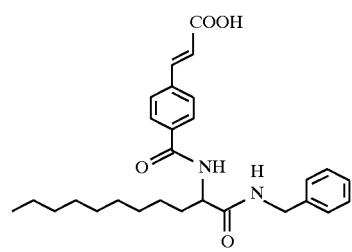

¹HNMR (CD₃OD): δ0.84 (t, 3H); 1.22–1.38 (m, 16H); 1.73–1.91 (m, 2H); 4.38 (ddd, 2H); 4.56 (q, 1H); 6.58 (d, 1H); 7.24–7.93 (m, 9H).
M.S. 436.3(calc.); 434.9(obs.)

EXAMPLE 3

PTP-1B Gene Cloning and Protein Purification

The following procedure was conducted for recombinant production and purification of protein tyrosine phosphatase PTP-1B, for use as a substrate in PTPase inhibition assays.

A. Production of a PTP-1B cDNA

A human placental cDNA library was synthesized in a 50 μl reaction containing 1 μg human placental poly(A)⁺ mRNA (Clontech, Palo Alto, Calif.), 4 μl random hexamer primers, 8 μl of 10 mM dNTPs (Pharmacia, Piscataway, N.J.), 1 μl (200 U/μl) Moloney murine leukemia virus reverse transcriptase (Gibco-BRL, Canada), 0.5 μl (26 U/μl) RNAsin (Promega, Madison, Wis.), and 12 μl 5×buffer (Gibco-BRL). The synthesis reaction was incubated at 37° C. for one hour and then heat inactivated at 95° C. for five minutes.

A PTP-1B cDNA was amplified, using polymerase chain reaction (PCR), from the cDNAs synthesized as described above. More particularly, based on the published sequence of PTB-1B, two PCR primers were synthesized to amplify a portion of the PTP-1B coding sequence known to encode a 321 amino acid fragment containing the PTP-1B catalytic domain and having PTPase activity. See Hoppe et al., *Eur. J. Biochem.*, 223:1069–77 (1994); Barford, D., et al., *J. Molec. Biol.*, 239:726–730 (1994); Chernoff et al., *Proc. Natl. Acad. Sci. USA*, 87:2735–2739 (1990); Charbonneau et al. *Proc. Natl. Acad. Sci. USA*, 86:5252–5256 (1989). The primers had the following respective sequences:
PTP-1B-A(5') (SEQ ID NO: 1)

5' CGCACTGGATCCTCATGGAGATGGAAAAGG 3'
PTP-1B-B(3') (SEQ ID NO: 2)
5' CTCCCTGAATTCCTAATTGTGTGGCTCCAGG 3'

The first primer, which hybridizes to the non-coding strand, corresponds to the 5' portion of the PTP-1B coding sequence and encodes a BamH I restriction site upstream of the initiation codon, to facilitate cloning. The second primer, which hybridizes to the coding strand, corresponds to the 3' portion of the PTB-1B fragment of interest, and encodes a stop codon and an EcoR I restriction site downstream from the stop codon.

A 100 ul PCR reaction mixture containing approx. 1 ug of the human placental cDNA library, 0.2 mM of each dNTP, 30 uM of each primer, 1×Amplitaq DNA polymerase buffer (Perkin-Elmer, Norwalk, Conn.), and 5 units Amplitaq DNA polymerase (Perkin-Elmer) was denatured at 94° C. for 5 minutes and then subjected to 25 cycles of amplification as follows: 1) 94° C. denaturation for 1 minute; 2) 55° C. annealing for 1 minute; and 3) 72° C. primer extension for 1 minute.

The PCR reaction product (992 bp) was digested with BamH I and EcoR I (New England Biolabs, Beverly, Mass.) to yield a 975 bp product encoding the 321 amino acid PTP-1B protein fragment, and having "sticky ends" to facilitate cloning.

B. Production of a PTP-1B expression vector

The 975 bp PTP-1B partial cDNA was purified by agarose gel electrophoresis and ligated into a BamH I/EcoR I-digested pGEX-3X plasmid vector (Pharmacia, Piscataway, N.J.). The pGEX vector is designed to produce a fusion of glutathione-S-transferase (GST) to a protein encoded by another DNA fragment inserted into the vector's cloning site. Complete sequencing of the insert of the resultant plasmid, designated pGEX-3X-PTP-1B, confirmed the identity of the PTP-1B cDNA, and insertion in the proper orientation and reading frame.

C. Expression and Purification of GST/PTP1B fusion protein

*E. coli* strain DH5α (Gibco-BRL) was transformed with plasmid pGEX-3X-PTP-1B following the supplier's transformation protocol and grown at 37° C. with vigorous shaking in Luria-Bertani broth supplemented with 100 μg/ml ampicillin. When the cultures reached an O.D.$_{600}$ of 0.7–1, production of the GST/PTP-1B fusion protein was induced with 0.1 mM IPTG (Isopropyl β-D-Thiogalactoside). After 3 additional hours of culturing at 37° C., the bacteria were pelleted by centrifugation.

The bacterial pellet was resuspended in 10×(w/v) lysis buffer consisting of 12.5 mM HEPES, 2 mM EDTA, pH 7.0, 15 mM β-mercaptoethanol (βme) and 1 mM PMSF. The lysate was sonicated (on ice) until slight clearing was observed (approx. three min.) and then centrifuged at 10,000 revolutions per minute (RPM) for 10 min. The supernatant was diluted 1:4 with buffer A (25 mM HEPES, pH 7.0, and 15 mM βme).

Primary purification was achieved using a 5 ml Hi-Trap pre-packed Q column (Pharmacia). After loading the diluted supernatant onto the column, the column was washed with 10 bed volumes of buffer A. The GST/PTP-1B fusion protein was then eluted using a linear gradient of Buffer A and Buffer B (buffer A+1M NaCl). Eluted fractions containing protein were identified by SDS-PAGE and Coomassie Blue staining (Pharmacia PhastSystem), and fractions containing PTP-1B activity were identified using the PTP-1B activity assay described below. Elution of the fusion protein occurred at about 30% Buffer B.

Fractions containing PTPase activity were pooled, diluted 1:4 with NET buffer (20 mM Tris, pH 8.8, 100 mM NaCl, 1 mM EDTA and 15 mM βme), and loaded onto a 10 ml GST-Sepharose 4B column (Pharmacia). After loading, the column was washed first with 3 bed volumes of NET buffer+1% NP40 (Sigma Chemical Co., St. Louis, Mo.), then with NET buffer until O.D. at 280 nm was basal. The GST/PTP-1B fusion protein was eluted from the column using 10 mM glutathione in 33 mM Tris, pH 8.8. Elution of proteins was monitored at O.D.$_{280}$ so and fractions were assayed for activity and run on SDS-PAGE as described above. PTP-1B fusion protein eluted after approx. 4–5 minutes (flow rate 1 ml/min.).

The GST/PTP-1B-containing fractions from the GST-Sepharose 4B purification were pooled, concentrated into a final storage buffer (0.2M NaCl, 25 mM HEPES, 1 mM EDTA, and 5 mM DTT, pH 7.0) using a 1 ml Hi-Trap Q column (pre-packed, Pharmacia), and stored at −80° C. (final concentration of 0.52 mg/ml). The foregoing procedure yielded approximately 5 mg of PTP-1B fusion protein per 500 ml of cultured cells, purified to substantial homogeneity as assessed by SDS-PAGE.

Assay of PTP-1B Activity

PTP-1B enzymatic activity of samples was assayed in microtiter plates as follows.

The protein concentration of the PTP-1B enzyme preparation was determined using the Bio-Rad Protein Assay kit (Bio-Rad, Hercules, Calif.). An aliquot from each sample was taken and diluted to 2 μg protein/ml using activity assay buffer (100 mM Sodium Acetate, pH 6.0, 1 mM EDTA, 0.1% TX-100 (International Biotechnologies, Inc.) and 15 mM βME) to form a PTP-1B stock solution.

A 100 μl reaction mixture was prepared containing 10 μl of the PTP-1B stock solution, 10 μl of 9 mM p-nitrophenylphosphate ((pNPP), Sigma Chemical Co., St. Louis, Mo.), and 80 μl of activity assay buffer. Reactions were mixed gently and incubated at 37° C. for 65 minutes. Enzymatic cleavage of phosphate from pNPP (a tyrosine phosphate analog) is marked by a colorimetric change in this substrate. See, e.g., Imbert et al., *Biochem J.*, 297:163–173 (1994); Ghosh and Miller, *Biochem. Biophys. Res. Comm.*, 194:36–44 (1993); Zanke et al., *Eur. J. Immunol*, 22:235–39 (1992).

Reactions were stopped by addition of 10 μl of a 0.5M NaOH/50% EtOH solution. To determine the enzymatic activity, absorbance readings of the reactions were measured at 405 nm using a Molecular Devices Thermomax Plate Reader (Menlo Park, Calif.).

EXAMPLE 4

HePTP Gene Cloning and Protein Purification

The following procedure was conducted to recombinantly produce and purify protein tyrosine phosphatase HePTP, for use as a substrate in PTPase inhibition assays.

A. Production of HePTP cDNA

A full-length cDNA clone of HePTP is produced by well-known methods described in the literature. See, e.g., Zanke et al., *Eur. J. Immunol.* 22:235–239 (1992). Alternatively, a HePTP cDNA is produced as described in the preceding example, using, e.g., 100 μg poly(A)$^+$ RNA and the primers described below for PCR amplification. A HePTP cDNA isolated by these or other means is used to recombinantly produce HePTP as described herein.

An isolated HePTP cDNA provided by Dr. Brent Zanke was amplified using PCR. Two PCR primers were synthesized to amplify the HePTP coding sequence, based on the published DNA sequence of this gene. Zanke et al. (1992), supra.:

NDE2760.3(N$_3$) (SEQ ID NO: 3)
5' CCTCCATATGGTCCAAGCCCATGG 3'
BAM2760.2(B$_2$) (SEQ ID NO: 4)
5' TTATGGATCCAGGGTGGCAGGGGTCAGG 3'

The first primer, which hybridizes to the non-coding strand, corresponds to the 5' portion of the HePTP coding sequence and encodes a Nde I restriction site upstream of the initiation codon, to facilitate cloning. The second primer, which hybridizes to the coding strand, corresponds to the 3' portion of the HePTP coding sequence and encodes a BamH I restriction site downstream from the HePTP termination codon.

An 87 ul PCR reaction mixture containing 200 ng of HePTP cDNA, 0.2 mM of each DNTP, 30 uM of each primer, 1×Vent DNA polymerase buffer, and 2 units Vent DNA polymerase (New England Biolabs) was amplified as follows: 1) 94° C. denaturation for 5 minutes; and 2) fifteen cycles of 94° C. denaturation for 1 minute, 55° C. annealing for 1 minute, and 72° C. extension for 1 minute.

B. Production of an HePTP expression vector

The resultant 1115 base pair PCR product was digested with BamH I and Nde I (New England Biolabs), gel-purified, and ligated into a BamH I/Nde I—digested pET12a expression vector (Novagen). Complete sequencing of the insert of the resultant plasmid, designated pET12a-HePTP, confirmed the identity of the HePTP cDNA and insertion in the proper orientation and reading frame.

C. Expression and Purification of recombinant HePTP protein

*E. coli* strain BL21(DE3) (Novagen, Madison, Wis.) was transformed with plasmid pET*12*a-HePTP and grown at 37° C. with vigorous shaking in Luria-Bertani broth supplemented with 100 μg/ml ampicillin. When the cultures reached an O.D.$_{600}$ of 0.7–1, production of HePTP protein was induced with 0.1 mM IPTG. After 3 additional hours of culturing at 37° C., the bacteria were pelleted.

The bacterial pellet was resuspended in 10×(w/v) lysis buffer consisting of 12.5 mM HEPES, 2 mM EDTA, pH 7.0, 15 mM βme, and 1 mM PMSF. The lysate was sonicated (on ice) until slight clearing was observed (approx. three minutes) and then centrifuged at 10,000 RPM for 10 min. The supernatant was diluted 1:4 with buffer A (25 mM HEPES, pH 7.0, and 15 mM βme).

Primary purification was achieved using an SP-Sepharose column (Pharmacia). After loading the diluted supernatant onto the column, the column was washed with 10 bed volumes of buffer A. The HePTP protein then was eluted using a linear gradient of Buffer A and Buffer B (Buffer A+1M NaCl). Eluted fractions containing protein were identified by SDS-PAGE and Coomassie Blue staining (Pharmacia PhastSystem); HePTP activity in fractions was determined using the HePTP activity assay described below. Elution of HePTP occurred at about 23–30% Buffer B.

Fractions containing PTPase activity were pooled, diluted 1:4 with TB buffer (20 mM Tris, pH 8, and 15 mM βme), and loaded into a 10 ml Q-Sepharose column (Pharmacia) for further purification. After loading, the column was washed with 3 bed volumes of TB buffer. HePTP protein was eluted from the column using a linear gradient of Buffer A and Buffer B as previously described, assaying fractions for protein content and PTPase activity as previously described. Elution of the HePTP occurred at about 25% Buffer B. The HePTP-containing fractions were pooled, concentrated into a final storage buffer (0.2M NaCl, 25 mM HEPES, 1 mM EDTA, and 5 mM DTT, pH 7.0) using a 1 ml Hi-Trap Q column (pre-packed, Pharmacia), and stored at −80° C. (final concentration 3.127 mg/ml). The procedure yielded approx. 5 mg HePTP protein per 2 liters of culture.

Assay of HePTP Activity

HePTP enzymatic activity was assayed as described above for PTP-1B, except that 20 mM pNPP was substituted for the 9 mM pNPP employed in the PTP-1B reactions.

EXAMPLE 5

In vitro PTPase Inhibition Assay

The ability of the compounds of the present invention, such as the cinnamic acid derivative compounds of Example 2, to inhibit the PTPase activity of PTP-1B and HePTP was determined using a modification of the PTP-1B and HePTP activity assays described in Examples 3 and 4.

First, 0.001 mmol of the cinnamic acid derivative (or other PTPase inhibitor compound) was dissolved in 100 ul of DMSO to create a 10 mM stock solution. The 10 mM stock solution was used to add varying concentrations (100 uM, 33 uM, 10 uM, 3 uM, 1 uM, 0.3 uM, 0.1 uM, 0.03 uM, 0.01 uM or 0.003 uM) of the inhibitor compound to a series of otherwise identical PTPase activity assay reactions (100 ul final volume in microtiter wells). Thus, each 100 ul reaction contained 10 ul PTPase enzyme stock solution (final PTP-1B or HePTP concentration of 20 ng/well), 70 ul activity assay buffer, 10 ul pNPP stock solution (final pNPP concentration of 0.9 mM for PTP-1B assay and 2 mM for HePTP assay), and 10 ul of the diluted inhibitor compound in DMSO. The GST/PTP-1B or HePTP enzyme was added to the reaction mixtures to begin the reactions, which were incubated at 37° C. for 65 min., stopped, and colorimetrically analyzed as described above. As positive and negative controls, reactions were performed containing 10 ul DMSO with no inhibitor compound, or containing the known PTPase inhibitor vanadate (final concentration 0.5 mM) substituted for the inhibitor compound of the invention.

The concentration of inhibitor compound required to inhibit 50% of the PTPase activity (IC50) was determined as follows. First, absorbance readings from the vanadate control reactions were treated as a baseline and subtracted from the absorbance readings of the experimental reactions. Then, for each reaction, a percent inhibition was calculated using the following formula:

$$100 \times [1-(O.D._{405} \text{ reaction}/O.D._{405} \text{ DMSO})]$$

For each inhibitor compound tested, an IC50 concentration was calculated from a best-fit computer analysis of the calculated percent inhibition for the various dilutions of the compound.

Inhibitor compounds having an IC50 less than 10 uM (an optimally less than 5 uM) for a particular PTPase were scored as highly effective inhibitors of that PTPase enzyme, and are preferred inhibitors of the present invention. Table 2 reports the IC50 concentration for a number of cinnamic acid derivative compounds of Formula II (FIG. 4) of the present invention.

TABLE 2

PTPase inhibitory activity in in vitro assay

| Cinnamic Acid Substitution | R1 | R2 | Mol. Wt. (Calc.) | Mol. Wt. (Obsd.) | HePTP IC50 ($\mu$M) | PTP1B IC50 ($\mu$M) |
|---|---|---|---|---|---|---|
| para- | Methyl | n-Butyl | 318.2 | 316.9 | 7.3 | 4.9 |
| para- | Methyl | t-butyl | 318.2 | 317.0 | 8.0 | 4.8 |
| para- | Methyl | $CH_2CO_2$Methyl | 334.1 | 333.0 | 8.3 | 3.9 |
| para- | Methyl | $CH_2CO_2$Ethyl | 348.2 | 346.9 | 6.3 | 3.8 |
| para- | Methyl | $CH_2CO_2H$ | 320.1 | 318.9 | 5.4 | 0.9 |
| para- | Methyl | Cyclohexyl | 344.2 | 342.9 | 5.7 | 3.9 |
| para- | Ethyl | n-Butyl | 332.2 | 331.0 | 5.2 | 3.0 |
| para- | Ethyl | 1,1,3,3-tetramethylbutyl | 388.3 | 387.0 | 8.9 | 7.4 |
| para- | Ethyl | t-butyl | 332.2 | 331.0 | 7.9 | 4.2 |
| para- | Ethyl | $CH_2CO_2$Methyl | 348.2 | 346.9 | 7.6 | 4.8 |
| para- | Ethyl | $CH_2CO_2$Ethyl | 362.2 | 360.9 | 6.0 | 4.4 |
| para- | Ethyl | $CH_2CO_2H$ | 334.2 | 332.9 | 3.6 | 1.6 |
| para- | Ethyl | Cyclohexyl | 358.3 | 356.9 | 4.6 | 3.4 |
| para- | Ethyl | Benzyl | 366.2 | 364.9 | 2.5 | 2.1 |
| para- | n-Propyl | n-Butyl | 346.2 | 344.9 | 6.5 | 4.4 |
| para- | n-Propyl | 1,1,3,3-tetramethylbutyl | 402.4 | 401.0 | 8.1 | 6.5 |
| para- | n-Propyl | t-butyl | 346.2 | 344.9 | 7.8 | 5.4 |
| para- | n-Propyl | $CH_2CO_2$Methyl | 362.2 | 360.9 | 6.8 | 4.9 |
| para- | n-Propyl | $CH_2CO_2$Ethyl | 376.2 | 374.9 | 5.6 | 4.8 |
| para- | n-Propyl | $CH_2CO_2H$ | 348.2 | 346.9 | 3.7 | 1.8 |
| para- | n-Propyl | Cyclohexyl | 372.3 | 371.0 | 5.1 | 4.0 |
| para- | n-Propyl | Benzyl | 380.3 | 379.0 | 4.2 | 3.9 |
| para- | n-Butyl | n-Butyl | 360.3 | 359.0 | 8.6 | 4.6 |
| para- | n-Butyl | 1,1,3,3-tetramethylbutyl | 416.4 | 415.0 | 8.9 | 4.5 |
| para- | n-Butyl | t-butyl | 360.3 | 359.0 | 7.9 | 5.1 |
| para- | n-Butyl | $CH_2CO_2$Methyl | 376.2 | 375.0 | 7.6 | 4.6 |
| para- | n-Butyl | $CH_2CO_2$Ethyl | 390.3 | 389.0 | 6.6 | 3.4 |
| para- | n-Butyl | $CH_2CO_2H$ | 362.2 | 360.9 | 4.6 | 1.9 |
| para- | n-Butyl | Cyclohexyl | 386.3 | 384.9 | 5.9 | 4.0 |
| para- | n-Butyl | Benzyl | 394.3 | 393.0 | 2.5 | 2.1 |
| para- | n-Hexyl | n-Butyl | 388.3 | 387.0 | 23.3 | 10.3 |
| para- | n-Hexyl | 1,1,3,3-tetramethylbutyl | 444.4 | 443.1 | 10.9 | 4.9 |
| para- | n-Hexyl | t-butyl | 388.35 | 387.0 | 8.5 | 5 |

TABLE 2-continued

PTPase inhibitory activity in in vitro assay

| Cinnamic Acid Substitution | R1 | R2 | Mol. Wt. (Calc.) | Mol. Wt. (Obsd.) | HePTP IC50 ($\mu$M) | PTP1B IC50 ($\mu$M) |
|---|---|---|---|---|---|---|
| para- | n-Hexyl | $CH_2CO_2$Methyl | 404.3 | 403.0 | 6.4 | 2.9 |
| para- | n-Hexyl | $CH_2CO_2$Ethyl | 418.3 | 417.0 | 6.2 | 2.9 |
| para- | n-Hexyl | $CH_2CO_2H$ | 390.2 | 389.0 | 3.6 | 1.1 |
| para- | n-Hexyl | Cyclohexyl | 414.4 | 413.0 | 5.5 | 3.2 |
| para- | n-Hexyl | Benzyl | 422.3 | 421.0 | 2.3 | 1.7 |
| para- | n-Heptyl | n-Butyl | 402.4 | 401.0 | 6.9 | 4.0 |
| para- | n-Heptyl | 1,1,3,3-tetramethylbutyl | 458.5 | 457.1 | 18.9 | 7.9 |
| para- | n-Heptyl | t-butyl | 402.4 | 401.0 | 8.2 | 5.2 |
| para- | n-Heptyl | $CH_2CO_2$Methyl | 418.3 | 416.9 | 5.7 | 2.9 |
| para- | n-Heptyl | $CH_2CO_2$Ethyl | 432.3 | 430.9 | 5.8 | 3.3 |
| para- | n-Heptyl | $CH_2CO_2H$ | 404.3 | 402.9 | 3.5 | 1.1 |
| para- | n-Heptyl | Cyclohexyl | 428.4 | 427.0 | 6.0 | 3.9 |
| para- | n-Heptyl | Benzyl | 436.4 | 434.9 | 3.2 | 2.6 |
| para- | Phenyl | n-Butyl | 380.3 | 379.0 | 7.2 | 3.8 |
| para- | Phenyl | 1,1,3,3-tetramethylbutyl | 436.4 | 434.9 | 8.8 | 3.4 |
| para- | Phenyl | t-butyl | 380.3 | 379.0 | 7.7 | 3.6 |
| para- | Phenyl | $CH_2CO_2$Methyl | 396.2 | 395.0 | 12.1 | 7.2 |
| para- | Phenyl | $CH_2CO_2$Ethyl | 410.2 | 408.9 | 10.1 | 5.9 |
| para- | Phenyl | $CH_2CO_2H$ | 382.2 | 380.9 | 5.5 | 2.8 |
| para- | Phenyl | Cyclohexyl | 406.3 | 404.9 | 6.0 | 3.6 |
| para- | Phenyl | Benzyl | 414.3 | 413.0 | 1.5 | 0.9 |
| para- | $PhCH_2CH_2$ | n-Butyl | 408.3 | 406.9 | 8.7 | 5.2 |
| para- | $PhCH_2CH_2$ | 1,1,3,3-tetramethylbutyl | 464.4 | 463.0 | 14 | 7.3 |
| para- | $PhCH_2CH_2$ | t-butyl | 408.3 | 407.0 | 13.4 | 10.5 |
| para- | $PhCH_2CH_2$ | $CH_2CO_2$Methyl | 424.3 | 422.9 | 8.2 | 5.3 |
| para- | $PhCH_2CH_2$ | $CH_2CO_2$Ethyl | 438.4 | 436.9 | 7.4 | 5.9 |
| para- | $PhCH_2CH_2$ | $CH_2CO_2H$ | 410.3 | 408.9 | 4.1 | 1.9 |
| para- | $PhCH_2CH_2$ | Cyclohexyl | 434.4 | 433.3 | 6.2 | 6.8 |
| para- | $PhCH_2CH_2$ | Benzyl | 442.3 | 440.9 | 1.6 | 2.6 |
| meta- | 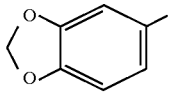 1,3 benzo-dioxolyl | n-Butyl | 424.5 | 423.0 | 9.0 | 1.9 |
| meta- | N-acetyl-3-indolyl | t-Butyl | 460.6 | 460.0 | 4.85 | |
| meta- | 3,4-dichloro phenyl | $CH_2COOH$ | 451.2 | 450.6 | 3.22 | |
| meta- | 4-hydroxy-3-methoxy phenyl | cyclohexyl | 451.5 | 451.0 | 5.0 | |
| ortho- | 3,4,5-trimethoxy phenyl | benzyl | 504.2 | 503.0 | 1.3 | 1.9 |

EXAMPLE 6

Synthesis and Screening of Additional Cinnamic Acid Derivative Compounds

Additional cinnamic acid derivative compounds were synthesized using an Ugi Reaction combinatorial synthesis, essentially as described in Example 2. Aldehyde compounds of formula 3 (FIG. 4) were selected to provide $R_1$=3-(3-trifluoromethyl) phenoxyphenyl; 4-(diethylamino) phenyl; 4-(methylthio) phenyl; 3-(4-butylphenoxy) phenyl; 3-(4-methoxyphenoxy) phenyl; 3-(4-chlorophenoxy)phenyl; 3-(3,4-dichlorophenoxy)phenyl; and 3-(3,5-dichlorophenoxy) phenyl. Seven of the eight commercially available isocyanide reagents described in Example 2 were employed (1,1,3,3-tetramethylbutyl isocyanide was not selected). Meta- and para- carboxylic acid t-butyl cinnamate were synthesized as described in Example 1 to provide the acid reagent of Formula 5.

The synthesized compounds of Formula II were screened for PTP-1B or HePTP inhibitory activity at an effective concentration of 10 $\mu$M, as described in Example 2. Since none of these compounds exhibited substantial PTPase inhibitory activity against these two enzymes in this initial screening, the reaction products were not further characterized.

EXAMPLE 7

Synthesis and Screening of Additional Cinnamic Acid Derivative Compounds

Additional cinnamic acid derivative compounds were synthesized using a combinatorial Ugi reaction essentially as described in Example 2. Referring again to FIG. 4, aldehyde reagents of formula 3 were selected to provide the following $R_1$ substituents:

3-(N-methylindolyl)
3-(N-acetylindolyl)
3-(Indolyl)
4-trifluoromethylphenyl
2-Naphthyl
1-Naphthyl
4-(dimethylamino) phenyl
3,4,5-trimethoxyphenyl
2,4,5-trimethoxyphenyl
2,4,6-trimethoxyphenyl
2,3,4-trimethoxyphenyl
2,4,6-trimethoxyphenyl
3,4,5-trihydroxyphenyl Seven of the eight commercially available isocyanide reagents described in Example 2 were selected to provide $R_2$ substituents (1,1,3,3-tetramethylbutyl isocyanide was not selected). Ortho- and para- carboxylic acid t-butyl cinnamates were synthesized as described in Example 1 to provide the acid reagent of Formula 5.

The synthesized compounds were screened for HePTP inhibitory activity at an effective concentration of 10 μM, as described in Example 2, and a number of the compounds exhibited substantial HePTP inhibitory activity. For example, reaction products wherein $R_1$=2,4,5-trimethoxyphenyl exhibited 60–65% HePTP inhibition where $R_2$=n-butyl, benzyl, or cyclohexyl; reaction products wherein $R_1$=2,4,6-trimethoxyphenyl exhibited 50–70% HePTP inhibition where $R_2$=t-butyl, cyclohexyl, or benzyl; reaction products wherein $R_1$=2,3,4-trimethoxyphenyl exhibited 40–55% HePTP inhibition where $R_2$=n-butyl, t-butyl, or benzyl.

At least one compound was selected for further analysis, resynthesized, and confirmed by mass spectrometry and NMR:

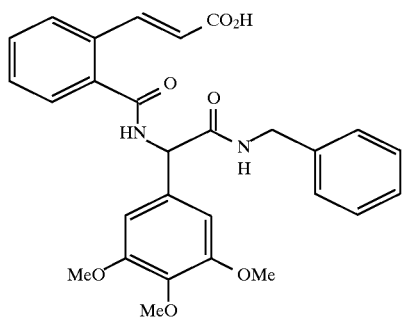

$^1$HNMR (CD$_3$OD): δ3.76–3.84 (3×S, 9H); 4.42 (m, 2H); 5.62 (s, 1H); 6.41 (d, 1H); 6.78 (s, 2H); 7.14–7.93 (m, 10H).

M.S. 504.2(calc.); 503.0 (obs.).

HePTPase inhibitory activity for this compound was determined as described in Example 5, and is reported in Table 2.

EXAMPLE 8

Synthesis and Screening of Additional Meta-Substituted Cinnamic Acid Derivative Compounds Additional meta-substituted cinnamic acid derivative compounds of the invention were synthesized by Ugi reaction and screened for PTPase inhibitory activity described in the preceding examples. NMR and Mass spectrometry data for four such compounds that were selected for further characterization are set forth below:

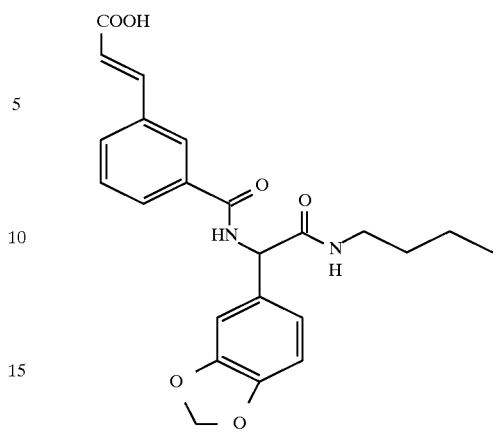

$^1$HNMR (CD$_3$OD): δ0.86 (t, 3H); 1.20–1.42 (m,4H); 3.16 (m,2H); 5.51 (s, 1H); 5.92 (s, 2H); 6.56 (d, 1H); 6.84 (d, 1H); 6.85 (s, 1H); 7.43 (t, 1H); 7.66 (d, 1H); 7.73 (d, 1H); 7.84 (d, 1H); 8.07 (s, 1H).

M.S. 424.5(calc.): 423.0(obs.)

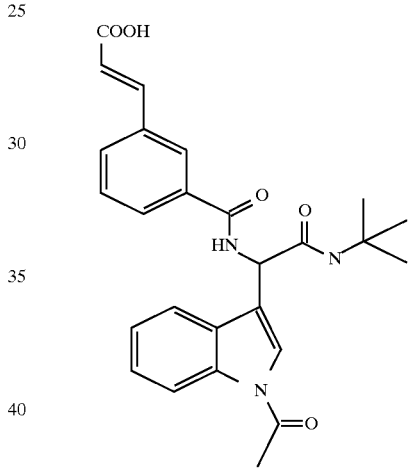

$^1$HNMR (CD$_3$OD): δ1.32 (s, 9H); 2.612 (s, 3H); 5.93 (s, 1H); 6.5 (d, 1H 7.22–8.26 (m, 11H).

M.S. 460.6 (calc.); 460.0(obs.)

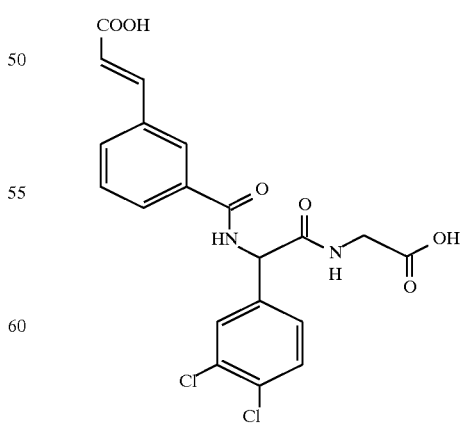

$^1$HNMR (CD$_3$OD): δ33.85(s, 2H); 5.78 (s, 1H); 6.58 (d, 1H); 7.41–8.12 (m, 8H).

M.S. 451.2(calc.): 450.6(obs.)

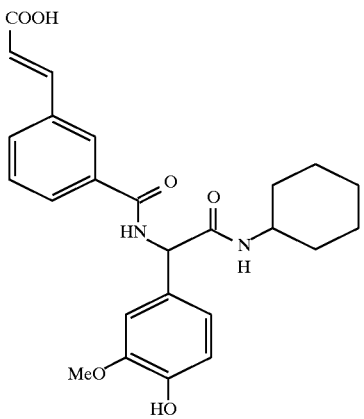

¹HNMR (CD₃OD): δ1.09–1.91 (m, 10H); 3.63 (m, 1H); 3.82 (s, 3H); 5.62 (s, 1H); 6.56 (d, 1H); 6.74 (d, 1H); 6.84 (d, 1H); 7.03 (s, 1H); 7.43 (t, 1H); 7.64 (d, 1H); 7.74 (d, 1H); 7.84 (d, 1H); 8.06 (s, 1H).

M.S. 451.5(calc.); 451.0(obs.)

The PTPase inhibitory activities of these four compounds against HePTP, determined as described in Example 5, are set forth in Table 2.

EXAMPLE 9

2-Furylacrylic Acid Derivative Synthesis and Initial Screening for PTPase Inhibitory Activity 2-Furylacrylic acid derivative compounds were synthesized using a combinatorial Ugi Reaction as described in Example 2, except that the following furylacrylic acid derivative, synthesized as described in Example 1, was employed as the carboxylic acid reagent:

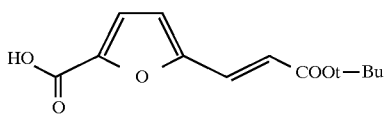

Thus, as depicted in FIG. 2, compounds having the following Formula (III) were synthesized by the combinatorial reaction:

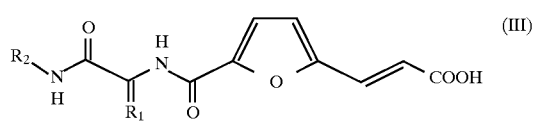

The synthesized compounds were screened at 5.0 μM concentrations for PTP-1B or HePTP inhibitory activity as described previously. The results of the screening assay, set forth in Table 3, provide an indication that furylacrylic acid derivatives are effective PTPase inhibitor compounds.

TABLE 3

Percentage of Inhibition of HePTP and PTP-1B at 5.0 μM of Furylacrylic Acid Derivatives of Formula III

| R1 | R2 | HePTP % of Inhib. | PTP-1B % of Inhib. |
|---|---|---|---|
| Methyl | n-Butyl | 13 | 55 |
| Methyl | t-butyl | 33 | 66 |
| Methyl | CH₂CO₂Methyl | 83 | 39 |
| Methyl | CH₂CO₂Ethyl | 29 | 68 |
| Methyl | CH₂CO₂H | 21 | 63 |
| Methyl | Cyclohexyl | 5.7 | 3.9 |
| Ethyl | n-Butyl | 34 | 68 |
| Ethyl | 1,1,3,3-tetramethylbutyl | 45 | 77 |
| Ethyl | t-butyl | 45 | 80 |
| Ethyl | CH₂CO₂Methyl | 37 | 75 |
| Ethyl | CH₂CO₂Ethyl | 37 | 75 |
| Ethyl | CH₂CO₂H | 42 | 77 |
| Ethyl | Cyclohexyl | 74 | 87 |
| Ethyl | Benzyl | 53 | 78 |
| n-Propyl | n-Butyl | 24 | 62 |
| n-Propyl | 1,1,3,3-tetramethylbutyl | 46 | 73 |
| n-Propyl | t-butyl | 36 | 58 |
| n-Propyl | CH₂CO₂Methyl | 40 | 69 |
| n-Propyl | CH₂CO₂Ethyl | 34 | 62 |
| n-Propyl | CH₂CO₂H | 37 | 66 |
| n-Propyl | Cyclohexyl | 65 | 74 |
| n-Propyl | Benzyl | 53 | 62 |
| n-Butyl | n-Butyl | 36 | 83 |
| n-Butyl | 1,1,3,3-tetramethylbutyl | 52 | 86 |
| n-Butyl | t-Butyl | 55 | 89 |
| n-Butyl | CH₂CO₂Methyl | 35 | 76 |
| n-Butyl | CH₂CO₂Ethyl | 48 | 84 |
| n-Butyl | CH₂CO₂H | 52 | 85 |
| n-Butyl | Cyclohexyl | 76 | 91 |
| n-Butyl | Benzyl | 59 | 82 |
| n-Hexyl | n-Butyl | 38 | 82 |
| n-Hexyl | 1,1,3,3-tetramethylbutyl | 51 | 83 |
| n-Hexyl | t-butyl | 41 | 76 |
| n-Hexyl | CH₂CO₂Methyl | 42 | 78 |
| n-Hexyl | CH₂CO₂Ethyl | 41 | 77 |
| n-Hexyl | CH₂CO₂H | 58 | 84 |
| n-Hexyl | Cyclohexyl | 74 | 88 |
| n-Hexyl | Benzyl | 56 | 74 |
| n-Heptyl | n-Butyl | 23 | 74 |
| n-Heptyl | 1,1,3,3-tetramethylbutyl | 48 | 83 |
| n-Heptyl | t-butyl | 44 | 79 |
| n-Heptyl | CH₂CO₂Methyl | 41 | 77 |
| n-Heptyl | CH₂CO₂Ethyl | 42 | 77 |
| n-Heptyl | CH₂CO₂H | 40 | 75 |
| n-Heptyl | Cyclohexyl | 67 | 83 |
| n-Heptyl | Benzyl | 45 | 68 |
| Phenyl | n-Butyl | 36 | 82 |
| Phenyl | 1,1,3,3-tetramethylbutyl | 51 | 82 |
| Phenyl | t-butyl | 47 | 81 |
| Phenyl | CH₂CO₂Methyl | 40 | 76 |
| Phenyl | CH₂CO₂Ethyl | 56 | 85 |
| Phenyl | CH₂CO₂H | 50 | 83 |
| Phenyl | Cyclohexyl | 76 | 88 |
| Phenyl | Benzyl | 57 | 69 |

EXAMPLE 10

PTPase inhibitory Activity of Commercially Available Acrylic Acids

The novel PTPase inhibitory activities of various commercially available aryl acrylic acids were demonstrated using the in vitro HePTP inhibition assay described above. As shown in Table 4, fifty micromolar concentrations of more than sixty such acids possessed measurable HePTP inhibitory activity. In addition to cinnamic acid and furylacrylic acid derivatives, thienyl acrylic acid and pyridyl acrylic acid derivatives were shown to possess measurable HePTP inhibitory activity. Collectively, this data provides an indication that aryl acrylic acids in addition to those specifically exemplified herein (e.g., having alternative aromatic moieties, substituents, and/or substitution patterns) and derivatives of the aryl acrylic acids specifically exemplified herein possess PTPase inhibitory activity.

TABLE 4

HePTP Inhibition Assay at 50 μM

| Aryl Acrylic Acid | % Inhibition of HePTP activity |
| --- | --- |
| 2-carboxy-cinnamic acid | 64.2 |
| 2-chlorocinnamic acid | 61.1 |
| 2-chloro-5-nitrocinnamic acid | 65.4 |
| 4-aminocinnamic acid | 45.2 |
| trans-cinnamic acid | 40.9 |
| a-cyano-3-hydroxy-cinnamic acid | 24.7 |
| a-cyano-4-hydroxy-cinnamic acid | 25.5 |
| trans-2,5-difluorocinnamic acid | 58.1 |
| trans-2,6-difluorocinnamic acid | 79.2 |
| 3,4-dihydroxycinnamic acid | 31.8 |
| trans-2,3-dimethoxycinnamic acid | 37.5 |
| trans-2,4-dimethoxycinnamic acid | 39.6 |
| 2,5-dimethoxycinnamic acid | 46.1 |
| 3,5-dimethoxy-4-hydroxy-cinnamic acid | 37.1 |
| 2-fluorocinnamic acid | 65.1 |
| '2-hydroxycinnamic acid | 59.1 |
| '3-hydroxycinnamic acid | 44.3 |
| '4-hydroxycinnamic acid | 47.8 |
| trans-4-hydroxy-3-methoxy-cinnamic acid | 32.6 |
| Alpha-fluorocinnamic acid | 31.5 |
| 3-methoxy cinnamic acid | 40.1 |
| 2-nitro cinnamic acid | 51.8 |
| '2-(trifluoromethyl)cinnamic acid | 34.4 |
| 2,4,5-trimethoxycinnamic acid | 45.2 |
| trans-5-bromo-2-methoxy-cinnamic acid | 50.6 |
| 4-formyl cinnamic acid | 79.4 |
| 2-methoxycinnamic acid | 50.2 |
| 3,4-difluorocinnamic acid | 48.1 |
| 3-bromocinnamic acid | 42.7 |
| 4-bromocinnamic acid | 45.1 |
| 3-chlorocinnamic acid | 47.1 |
| 4-chlorocinnamic acid | 49.8 |
| trans-2,4-dichlorocinnamic acid | 73.2 |
| 2,6-dichlorocinnamic acid | 51.1 |
| 3,4-dichlorocinnamic acid | 67.3 |
| trans-2,4-difluorocinnamic acid | 58.3 |
| trans-3,4-difluorocinnamic acid | 44.1 |
| 3,5-difluorocinnamic acid | 35.4 |
| 3,4-dimethoxycinnamic acid | 35.6 |
| 3,5-dimethoxycinnamic acid | 29.3 |
| alpha-phenylcinnamic acid | 22.2 |
| trans-3-fluorocinnamic acid | 45.9 |
| 4-fluorocinnamic acid | 53.6 |
| 3-hydroxy-4-methoxycinnamic acid | 54.5 |
| 4-methoxy cinnamic acid | 71.1 |
| 4-methyl cinnamic acid | 65.4 |
| 3-nitro cinnamic acid | 46.1 |
| 4-nitro cinnamic acid | 67.4 |
| 2,3,4,5,6-pentafluoro-cinnamic acid | 42.9 |
| 1,4-phenylenediacrylic acid | 91.1 |
| 3-(trifluoromethyl)cinnamic acid | 37.9 |
| trans-4-(trifluoromethyl)cinnamic acid | 74.8 |
| 3,4,5-trimethoxycinnamic acid | 44.3 |
| trans-3-fluorocinnamic acid | 45.1 |
| alpha-(t-Bu)-hydrocinnamic acid | 24.5 |
| 5-hydroxymethylfurylacrylic acid | 21.6 |
| trans-3-furylacrylic acid | 79.6 |
| trans-3-(pyridyl)acrylic acid | 32.3 |
| 3-(2-thienyl)acrylic acid | 61.9 |
| 4-chloro-beta-methylcinnamic acid | 24.2 |
| Trans-3-furanacrylic acid | 34.3 |
| 1-Transcinnamoyl immidazole | 28.1 |

It will be apparent from the data presented in Table 4 that the present invention provides both novel acrylic acid compounds and new uses for acrylic acid compounds of the formula (AA)

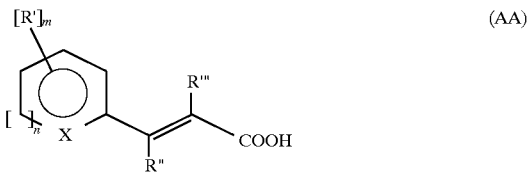

wherein X and n are defined as in formula (A), supra, wherein m is an integer from 0 to 4, and wherein R', R" and R'" represent hydrogen(s) and/or one or more independently selected appropriate substituents (e.g, substituents comprising electron withdrawing and/or donating groups, polar groups, cationic and/or anionic groups, acidic and/or basic groups, hydrophilic and/or hydrophobic groups, hydrogen bond donors or acceptors, aromatic groups, etc.) of the aromatic ring (pyridyl, furyl, phenyl, thiophenyl) or alkene carbons selected to optimize the potency, selectivity, specificity, etc. of such inhibitor compounds towards different PTPase enzymes. See generally, Roberts and Price, *The Role of Organic Chemistry in Drug Research*, Academic Press (1985); Silverman, R. B., *The Organic Chemistry of Drug Design and Drug Action*, Academic Press, 1992.

EXAMPLE 11

Tripeptide Amide Cinnamic Acid Derivatives

A library of tripeptide amide cinnamic acid derivatives was synthesized and assayed for PTPase inhibitory activity.

Library Design

A library of tripeptide amides acylated at the N-terminus with p-carboxycinnamate, having the general formula IV (wherein $A_1$, $A_2$, and $A_3$ represent amino acid side chains)

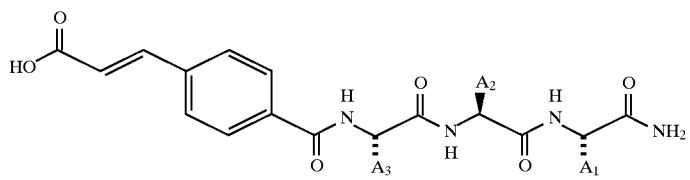

(IV)

was synthesized by well-known means. See Knorr et al., *Tetrahedron Lett.*, 30:1927–30 (1989). More particularly, the carboxylic acid group of a first amino acid moiety (having amino acid side chain $A_1$) was attached to a commercially-available resin substrate having an amine linkage group; thereafter, two additional amino acid moieties (having side chains $A_2$ and $A_3$) were sequentially coupled to the first amino acid. A cinnamic acid moiety was attached to the third amino acid moiety by reaction with a carboxylic acid reagent described in Example 1. Finally, the resin substrate and t-butyl protective group of the cinnamic acid moiety were removed by treatment with dry acid.

It can be seen that the library compounds are of the formula (AA), supra, wherein one R' substituent is a tripeptide amide and the remaining R', R", and R'" are hydrogens. Similarly, it can be seen that the library compounds are of the formula (I), supra, wherein $R_3$ of formula (1) has the formula (IR) and $R_1$ and $R_2$ are independently selected as described, supra. Amino acid substituents of the tripeptide amide were selected to create a library of compounds having a variety of side chain functionality. In particular, leucine (L) was selected for lypophilicity, tyrosine (Y) for aromatic structure, glutamate (E) for anionic charge, lysine (K) for cationic character, and glycine (G) for conformational flexibility. The library contained all 125 unique tripeptide amide compounds that could be synthesized using the five selected amino acids.

Inhibition Assay Results

The 125 compound library was assayed for PTP-1B inhibitory activity as described herein, using 10 mM final concentrations of each tripeptide amide compound, and the compounds were rank-ordered based upon their observed inhibitory activity. FIG. 5 depicts the percent inhibition of the twelve best and worst PTB-1B inhibitors of the library. The most potent inhibition of PTP-1B was observed for the compounds Cinn-GEL (96%) and Cinn-GEE (95%), the structures of which are depicted below:

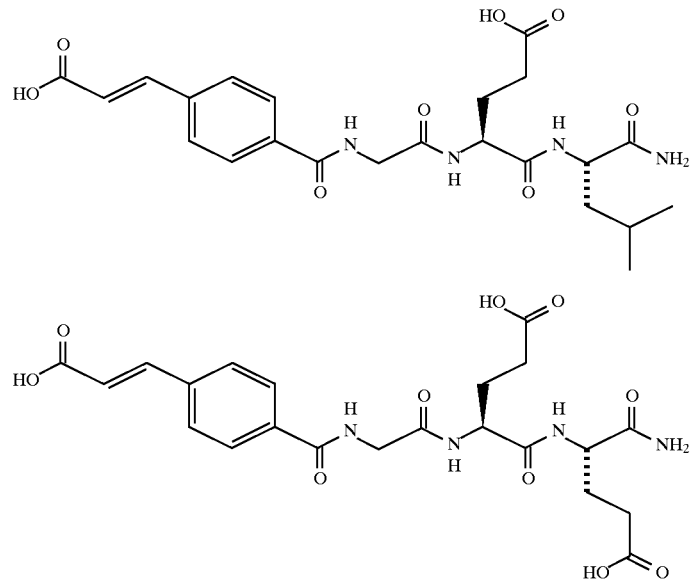

Analysis of the entirety of the PTPase inhibition data from the library provides significant guidance for design of effective PTP-1B inhibitors. For example, a conspicuous abundance of glutamate residues was observed in the top ten percent (12 compounds) of the PTP-1B inhibitors. More subtle was a positional preference observed for this residue. Eight out of the top twelve compounds have glutamates in the 3rd position, adjacent to the cinnamate cap. However, the two most potent inhibitors lack this positional preference.

Compounds having residues other than glutamate in the first and second positions still possessed significant PTPase inhibitory activity, with the notable exception of lysine, which residue was not present in the any of the most active sequences in this library. In fact, lysine appears deleterious to inhibitory activity, being abundant in the poorest inhibitors of the library. Thus, ligand charge is influential in determining a compound's PTP-1B inhibitory activity.

The influence of amino acid substituent charge on PTP-1B inhibitory activity is not unexpected when considering the structural data available for PTP-1B. Electron density maps of the protein surface surrounding the cavity containing the putative PTP-1B active site reveals a plethora of positively charged residues.

Kinetic analysis of the two best and worst tripeptide amide compounds, purified by reverse-phase HPLC, was consistent with the initial screening data. The compounds Cinn-GEL and Cinn-GEE had $K_i$ of 490 nM and 79 nM, respectively. Both compounds were competitive with pNPP substrate. In contrast, the two worst inhibitors, Cinn-LYK and Cinn-LGK, had IC50's of 49 µM and 46 µM, and showed mixed non-competitive behavior. Thus, there appears to be about a 1000-fold range of activity in the library. Similar ranges in activity have been observed within this library of inhibitors against other tyrosine phosphatases.

The foregoing example demonstrates that a relatively rapid screening procedure, using a relatively small library of selectively designed compounds (125 compounds) was sufficient to provide useful guidance for the design of effective inhibitors of individual PTPase enzymes.

EXAMPLE 12

MLR Cell Growth Inhibition Assay

The immunomodulatory properties of compounds of the present invention were demonstrated using the Mixed Lymphocyte Reaction (MLR) Assay. See Mishell & Shiigi, *Selected Methods in Cellular Immunology*. New York: W. H. Freeman and Co., pp. 163–64 (1980). See generally, Sasaki et al., *J. Antibiotics*, 47:208–215 (1995); Coligan et al. (eds.), *Current Protocols in Immunology*. New York: John Wiley & Sons, Inc., Vol. 1, Chapt. 3, Section 3.12, National Institute of Health, (1991); Abbas et al., *Cellular and Molecular Immunology*. Philadelphia: W. B. Saunders Co., pp. 99–104 (1991).

Spleens were removed from Balb C and C57BL6 mice, two distinct, inbred strains. In a tissue culture hood, the spleens were gently mashed through a fine screen into Hanks Balanced Saline Solution (Bio Whittaker 10-5088) media in a 10 cm petri dish. The red blood cells were lysed from the preparations by hypotonic shock, and then 10×concentrated PBS solution was added to restore osmolarity, followed by 4 ml of Hank's Balanced Saline Solution (BSS). The cell preparations were then pipetted up and down; dead red cells were allowed to stick to the side of the pipette. Cells were then washed twice in BSS.

A small number ($2 \times 10^7$) of Balb C cells (for background control) and all C57BL6 cells were irradiated with 2000 rads, to extinguish cell proliferation. These damaged cells (the stimulator cells) and the non-irradiated Balb C cells (the responder cells) were each resuspended in Iscove's media with 10% fetal calf serum, 1% L-glutamine, 10 µM βme and 100 g/ml each of penicillin /streptomycin.

MLR reactions (final volume~150 µl) were prepared in triplicate in 96-well flat-bottom microtiter plates as follows. In each well, $5 \times 10^5$ responder cells in 50 µl; $5 \times 10^5$ irradiated stimulator cells in 50 µl; and 50 µl of a diluted inhibitor compound of the invention were added. The inhibitor compounds were first dissolved in DMSO to form a 100 mM stock solution, and then added to wells at final concentrations of 1500, 500, 166, 55, 18, and 6 micromolar. For negative controls, reactions were performed wherein 50 µl of media alone or DMSO alone was substituted for the inhibitor compound. For positive controls, titrations with the MLR inhibitor Cyclosporin A were conducted.

Cultures were incubated at 37° C. with 5% $CO_2$ for four days. In co-culture, responder cells recognize the foreign MHC molecules of stimulator cells and begin to proliferate and mount an immune response. To assay the growth-inhibitory properties of the inhibitor compounds, each well was pulsed with 1 µCi ($^3$H)-Thymidine on day four. On day five, 16–18 hours after ($^3$H)-Thymidine addition, plates were harvested onto filter mats using a 96-well harvester and counted on a Packard Matrix gas phase scintillation counter.

To measure background, negative controls were conducted substituting the irradiated Balb C spleen cells for stimulator cells.

For each triplicate set of scintillation counter data, a mean and standard deviation was determined. The amount of an inhibitor required to reduce ($^3$H)-Thymidine incorporation by 50% (IC50 concentration) was graphically determined from the scintillation counter data. Table 5 reports the IC50 concentrations for a number of cinnamic acid derivative compounds (general Formula II) of the present invention. Compounds having an IC50≦100 µM were scored as highly effective inhibitors in the MLR assay.

TABLE 5

| PTPase Inhibitory Activity in Whole Cell Assay | | | |
|---|---|---|---|
| Cinnamic Acid substitution | R1 | R2 | IC50(uM) |
| para- | n-Butyl | n-Butyl | 91 |
| para- | Phenyl | 1,1,3,3-tetramethylbutyl | 8.0 |
| para- | n-Hexyl | Methyl | 13 |
| para- | n-Hexyl | $CH_2CO_2$Ethyl | 28 |
| para- | Phenyl | $CH_2CO_2$Ethyl | 31 |
| para- | n-Heptyl | Benzyl | 29 |
| para- | $PhCH_2CH_2$ | Benzyl | 36 |

While the present invention has been described in terms of specific embodiments, it is understood that variations and modifications will occur to those skilled in the art. For example, PTPase modulating compounds of the present invention have asymmetric centers and may occur as racemates, racemic mixtures, and as individual enantiomers or diastereoisomers, with all isomeric forms being included in the present invention as well as mixtures thereof.

The invention includes within its scope pharmaceutically acceptable salts, particularly where a basic or acidic group is present in a compound according to invention therein. For example, when an acidic substituent, such as —COOH, is present, the ammonium, sodium, potassium, calcium and the like salts, are contemplated as preferred embodiments for administration to a biological host. When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a preferred form for administration to a biological host.

Similarly, where an acid group is present, then pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

In addition, some of the phosphatase modulating compounds of the instant invention may form solvates with water or common organic solvents. Such solvates are encompassed within the scope of the invention.

The invention further includes compositions, e.g., pharmaceutical compositions, comprising phosphatase modulating compounds of the invention. By pharmaceutical composition is meant a composition that may be administered to a mammalian host, e.g., orally, topically, parenterally, by inhalation spray, or rectally, in unit dosage formulations containing conventional non-toxic carriers, diluents, adjuvants, vehicles and the like. The term parenteral as used herein includes subcutaneous injections, intravenous, intramuscular, intracisternal injection or infusion techniques.

The pharmaceutical compositions containing a PTPase modulating compound may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelating capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions may also be in the form of suppositories for rectal administration of the PTPase modulating compound. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols, for example.

For topical use, creams, ointments, jellies, solutions of suspensions, etc., containing the PTPase modulating compounds are contemplated. For purposes of this application, topical application shall include mouth washes and gargles.

Accordingly, only such limitations as appear in the appended claims should be placed on the invention.

What is claimed is:

1. A protein tyrosine phosphatase activity modulating compound having the formula (I):

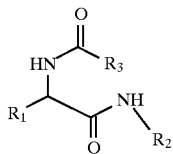

(a) wherein at least one of $R_1$, $R_2$ and $R_3$ has the formula (IR):

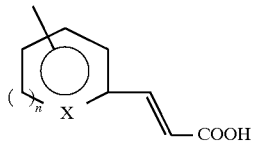

wherein n=0 or 1, X is selected from the group consisting of N and CH when n=1, and X is selected from the group consisting of O and S when n=0; and (b) wherein the remaining of $R_1$, $R_2$ and $R_3$ are independently selected from the group consisting of
   (i) hydrogen, $C_{1-11}$ alkyl,
   (ii) substituted $C_{1-11}$ alkyl, wherein the substituent is selected from the group consisting of hydroxy, halo, mercapto, amino, carboxy, carbamoyl, guanidino, aryl, hydroxyphenyl, $C_{1-6}$ alkyloxy, $C_{1-6}$ alkylthio, $C_{1-6}$ alkylamino, phenyl $C_{1-6}$ alkyloxy, phenyl $C_{1-6}$ alkylthio and phenyl $C_{1-6}$ alkylamino;
   (iii) aryl,
   (iv) $C_{1-11}$ alkyl aryl;
   (v) mono-, di- and tri-substituted aryl, wherein the substituents are independently selected from $C_{1-6}$ alkyl, trifluoromethyl, hydroxy, halo, $C_{1-6}$ alkyloxy, $C_{1-6}$ alkylthio, amino, $C_{1-6}$ alkylamino, amino $C_{1-6}$ alkyl, $C_{1-6}$ alkylcarbonyl, $C_{1-6}$ alkylcarbonylamino, $C_{1-6}$ alkylaminocarbonyl, carboxy, and carboxy $C_{1-6}$ alkyl; and
   (vi) $CH_2COX'R_4$, wherein X' is oxygen or NH and $R_4$ is independently selected from hydrogen, $C_1$–$C_{11}$ alkyl, aryl, and $C_1$–$C_{11}$ alkyl aryl;

wherein the aryl of (ii), (iii), (iv), (v), and (vi) are independently selected from the group consisting of phenyl, naphthyl, pyridyl, furyl, pyrryl, thienyl, isothiazolyl, imidazolyl, benzimidazolyl, tetrazolyl, pyrazinyl, pyrimidyl, quinolyl, isoquinolyl, benzofuryl, benzothienyl, pyrazolyl, indolyl, benzodioxolyl, piperonyl, isoindolyl, purinyl, carbazolyl, isoxazolyl, thiazolyl, oxazolyl, benzthiazolyl, and benzoxazolyl; and (c) wherein when $R_3$ of Formula (I) has the formula (IR), $R_2$ may further be of the formula (B):

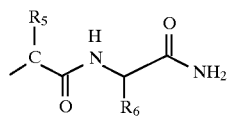

wherein $R_5$ and $R_6$ are independently selected from the group consisting of (b) (i) and (b) (ii);

or a pharmaceutically acceptable salt, ester, or solvate of said compound.

2. A protein tyrosine phosphatase inhibitor compound of claim 1 wherein $R_3$ of Formula (I) has the formula:

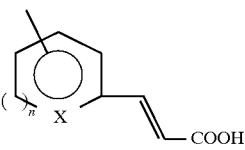

3. A protein tyrosine phosphatase inhibitor compound of claim 2 wherein $R_2$ is of the formula (B):

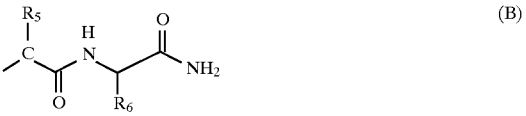

and wherein $R_1$, $R_5$, and $R_6$ are independently selected from the group consisting of:
   (i) hydrogen, $C_{1-11}$ alkyl, and
   (ii) substituted $C_{1-11}$ alkyl, wherein the substituent is selected from the group consisting of hydroxy, halo, mercapto, amino, carboxy, carbamoyl, guanidino, aryl, hydroxyphenyl, $C_{1-6}$ alkyloxy, $C_{1-6}$ alkylthio, $C_{1-6}$ alkylamino, phenyl $C_{1-6}$ alkyloxy, phenyl $C_{1-6}$ alkylthio and phenyl $C_{1-6}$ alkylamino.

4. A protein tyrosine phosphatase inhibitor compound of claim 2 of the formula:

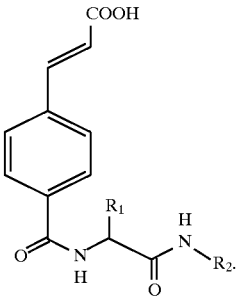

5. A protein tyrosine phosphatase inhibitor compound of claim 2 wherein $R_1$ and $R_2$ are independently selected form the group consisting of:
   (i) hydrogen, $C_{1-11}$ alkyl,
   (ii) substituted $C_{1-11}$ alkyl, wherein the substituent is selected from the group consisting of hydroxy, halo, mercapto, amino, carboxy, carbamoyl, guanidino, aryl, hydroxyphenyl, $C_{1-6}$ alkyloxy, $C_{1-6}$ alkylthio, $C_{1-6}$ alkylamino, phenyl $C_{1-6}$ alkyloxy, phenyl $C_{1-6}$ alkylthio and phenyl $C_{1-6}$ alkylamino;
   (iii) aryl,
   (iv) $C_{1-11}$ alkyl aryl;
   (v) mono-, di- and tri-substituted aryl, wherein the substituents are independently selected from $C_{1-6}$ alkyl, trifluoromethyl, hydroxy, halo, $C_{1-6}$ alkyloxy, $C_{1-6}$ alkylthio, amino, $C_{1-6}$ alkylamino, amino $C_{1-6}$ alkyl, $C_{1-6}$ alkylcarbonyl, $C_{1-6}$ alkylcarbonylamino, $C_{1-6}$ alkylaminocarbonyl, carboxy, and carboxy $C_{1-6}$ alkyl; and
   (vi) $CH_2COX'R_4$, wherein X' is oxygen or NH and $R_4$ is independently selected from hydrogen, $C_{1-11}$ alkyl, aryl, and $C_{1-11}$ alkyl aryl.

6. A protein tyrosine phosphatase inhibitor compound of claim 4 or 5 wherein $R_1$ is selected from the group consisting of hydrogen, unsubstituted $C_{1-11}$ alkyl, phenyl substituted $C_{1-11}$ alkyl, and phenyl.

7. A protein tyrosine phosphatase inhibitor compound of claim 6 wherein $R_2$ is selected from the group consisting of hydrogen, $C_{1-11}$ alkyl, phenyl substituted $C_{1-11}$ alkyl; and $CH_2COOR_4$, wherein $R_4$ is selected from hydrogen and $C_1$–$C_{11}$ alkyl.

8. A protein tyrosine phosphatase inhibitor compound of claim 4 or 6 wherein $R_2$ is selected from the group consisting of hydrogen, $C_{1-11}$ alkyl, phenyl substituted $C_{1-11}$ alkyl; and $CH_2COOR_4$, wherein $R_4$ is selected from hydrogen and $C_1$–$C_{11}$ alkyl.

9. A protein tyrosine phosphatase inhibitor compound of claim 5 wherein $R_1$ is selected from the group consisting of aryl, and mono-, di- and tri-substituted aryl.

10. A protein tyrosine phosphatase inhibitor compound of claim 9 wherein $R_2$ is selected from the group consisting of hydrogen, $C_{1-11}$ alkyl, phenyl substituted $C_{1-11}$ alkyl; and $CH_2COOR_4$, wherein $R_4$ is selected from hydrogen and $C_1$–$C_{11}$ alkyl.

11. A protein tyrosine phosphatase inhibitor compound of claim 10 wherein $R_1$ is selected from the group consisting of 1,3-benzodioxolyl, N-acetyl-3-indolyl, 3,4-dichlorophenyl, 4-hydroxy-3-methoxyphenyl, and 3,4,5-trimethoxyphenyl.

12. A protein tyrosine phosphatase inhibitor compound of claims 1, 2, 3, 5, 9, 10, or 11 wherein n=1 and X=CH.

13. A protein tyrosine phosphatase inhibitor compound of claim 10 having the formula:

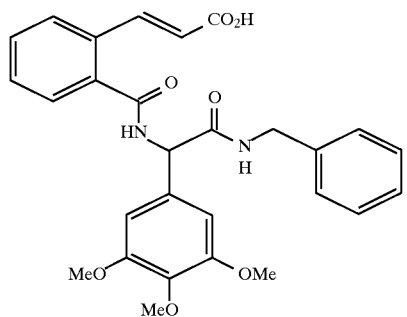

14. A protein tyrosine phosphatase inhibitor compound of claim 10 having the formula:

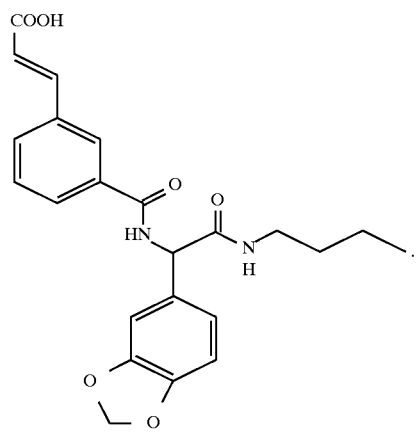

15. A protein tyrosine phosphatase inhibitor compound of claim 10 having the formula:

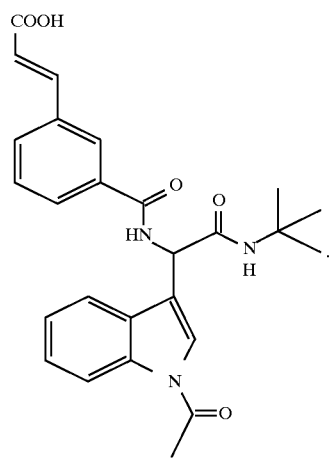

16. A protein tyrosine phosphatase inhibitor compound of claim 10 having the formula:

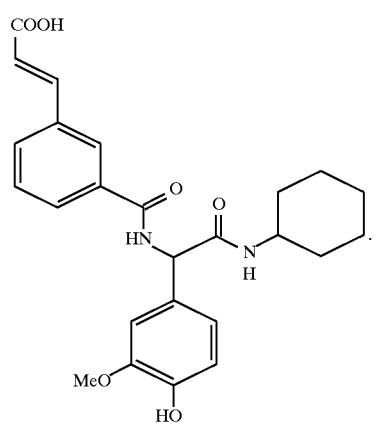

17. A protein tyrosine phosphatase inhibitor compound of claim 10 having the formula:

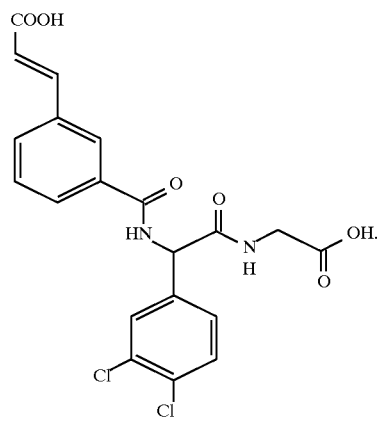

18. A protein tyrosine phosphatase inhibitor compound of claim 1 having the formula:

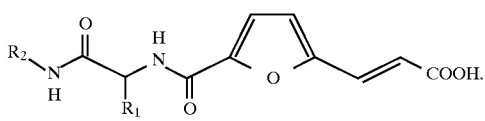

19. A protein tyrosine phosphatase inhibitor compound of claim wherein $R_1$ is selected from the group consisting of hydrogen, unsubstituted $C_{1-11}$ alkyl, phenyl substituted $C_{1-11}$ alkyl, and phenyl.

20. A protein tyrosine phosphatase inhibitor compound of claim 18 or 19 wherein $R_2$ is selected from the group consisting of hydrogen; $C_{1-11}$ alkyl, phenyl substituted $C_{1-11}$ alkyl; and $CH_2COOR_4$, wherein $R_4$ is selected from hydrogen and $C_1$–$C_{11}$ alkyl.

21. A composition comprising a protein tyrosine phosphatase modulating compound having the formula (AA):

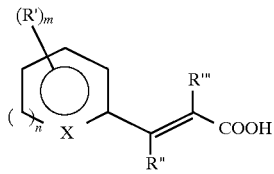

(a) wherein n=0 or 1,
  (i) when n=1, X is selected from the group consisting of N and CH, and
  (ii) when n=0, X is selected from the group consisting of O and S;
(b) wherein m is an integer from 1 to 4, and each R' is independently selected from the group consisting of halo, nitro, amino, hydroxy, carboxy, $C_{1-11}$ alkyl, carboxy $C_{1-6}$ alkyl —CH=CHCOOH, $C_{1-6}$ alkyloxy, trihalomethyl, formyl, $C_{1-6}$ alkylcarbonyl, and hydroxy $C_{1-6}$ alkyl; and
(c) wherein R" is a member selected from the group consisting of hydrogen, halo, phenyl and $C_{1-11}$ alkyl and R'" is selected from the group consisting of hydrogen, halo, cyano, phenyl, and $C_{1-11}$ alkyl;
or a pharmaceutically acceptable salt, ester, or solvate of said compound; said compound or salt, ester or solvate thereof being in admixture with a pharmaceutically acceptable diluent, adjuvent, or carrier.

22. The composition of claim 21 wherein each R' is independently selected from the group consisting of halo, nitro, amino, hydroxy, carboxy, methoxy, triflouromethyl, formyl, methyl, and hydroxymethyl.

23. The composition of claim 21 or 24 wherein R" is hydrogen.

24. The composition of claim 23 wherein R'" is hydrogen.

25. A composition comprising a protein tyrosine phosphatase modulating compound having the formula:

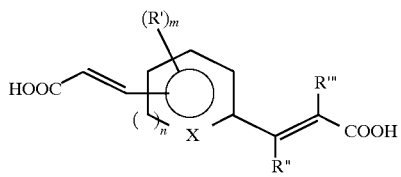

(a) wherein n=0 or 1,
  (i) when n=1, X is selected from the group consisting of N and CH, and
  (ii) when n=0, X is selected from the group consisting of O and S;
(b) wherein m is an integer from 0 to 3 and each R' is independently selected from the group consisting of halo, nitro, amino, hydroxy, carboxy, $C_{1-11}$ alkyl, carboxy $C_{1-6}$ alkyl, $C_{1-6}$ alkyloxy, trihalomethyl, formyl, $C_{1-6}$ alkylcarbonyl, and hydroxy $C_{1-6}$ alkyl; and
(c) wherein R" and R'" are independently selected from the group consisting of hydrogen, halo, cyano, phenyl, and $C_{1-11}$ alkyl;
or a pharmaceutically acceptable salt, ester, or solvate of said compound; said compound or salt, ester or solvate thereof being in admixture with a pharmaceutically acceptable diluent, adjuvent, or carrier.

26. The composition of claim 2 wherein each of R" and R'" is hydrogen.

27. A method for modulating or inhibiting the activity of PTPase, which comprises contacting an effective modulating or inhibitory amount of a compound selected from the group consisting of those defined in claims 1 or 21 with said PTPase.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CGCACTGGAT CCTCATGGAG ATGGAAAAGG    30

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

CTCCCTGAAT TCCTAATTGT GTGGCTCCAG G    31

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CCTCCATATG GTCCAAGCCC ATGG    24

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

TTATGGATCC AGGGTGGCAG GGGTCAGG    28